United States Patent
Iwasaki et al.

(10) Patent No.: US 11,493,571 B2
(45) Date of Patent: Nov. 8, 2022

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Tokyo (JP); Satoshi Shirotori, Kanagawa (JP); Akira Kikitsu, Kanagawa (JP); Yoshihiro Higashi, Ishikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 17/395,623

(22) Filed: Aug. 6, 2021

(65) Prior Publication Data

US 2022/0120830 A1 Apr. 21, 2022

(30) Foreign Application Priority Data

Oct. 16, 2020 (JP) .............................. JP2020-174624

(51) Int. Cl.
| | | |
|---|---|---|
| *G11C 11/16* | (2006.01) | |
| *G01R 33/09* | (2006.01) | |
| *G01R 15/20* | (2006.01) | |
| *A61B 5/245* | (2021.01) | |

(52) U.S. Cl.
CPC ......... *G01R 33/093* (2013.01); *G01R 15/205* (2013.01); *A61B 5/245* (2021.01)

(58) Field of Classification Search
CPC ...... G01R 33/093; G01R 15/205; A61B 5/245
See application file for complete search history.

(56) References Cited

U.S. PATENT DOCUMENTS

| | | | |
|---|---|---|---|
| 10,916,281 B2* | 2/2021 | Sugiyama | ............. G11C 11/161 |
| 2018/0174635 A1* | 6/2018 | Yoda | .................... G11C 11/1673 |
| 2018/0271395 A1 | 9/2018 | Iwasaki et al. | |
| 2020/0035280 A1* | 1/2020 | Sugiyama | ........... G11C 11/1675 |
| 2021/0027822 A1* | 1/2021 | Kim | ..................... G11C 11/1657 |

FOREIGN PATENT DOCUMENTS

| | | |
|---|---|---|
| JP | 2018-155719 | 10/2018 |
| WO | WO 2019/239933 | 12/2019 |

* cited by examiner

*Primary Examiner* — Alesa Allgood
(74) *Attorney, Agent, or Firm* — Finnegan, Henderson, Farabow, Garrett & Dunner, LLP

(57) ABSTRACT

According to one embodiment of the invention, a magnetic sensor includes a first element part. The first element part includes a first magnetic element, first and s second structures, a first magnetic member, and a second magnetic member. A direction from the first magnetic layer toward the first counter magnetic layer is along a first direction. The first structure includes a first side magnetic layer. The second structure includes a second side magnetic layer. The first magnetic element is between the first structure and the second structure in a second direction crossing the first direction. The first magnetic element is separated from the first side magnetic layer and the second side magnetic layer. A direction from the first side magnetic layer toward the first magnetic member is along the first direction. A direction from the second side magnetic layer toward the second magnetic member is along the first direction.

19 Claims, 21 Drawing Sheets

Hsig=0

+Hsig

-Hsig

MAGNETIC SENSOR AND INSPECTION DEVICE

CROSS-REFERENCE TO RELATED APPLICATIONS

This application is based upon and claims the benefit of priority from Japanese Patent Application No. 2020-174624, filed on Oct. 16, 2020; the entire contents of which are incorporated herein by reference.

FIELD

Embodiments of the invention relate generally to a magnetic sensor and an inspection device.

BACKGROUND

There is a magnetic sensor using on a magnetic layer. There is an inspection device using the magnetic sensor. It is desired to improve the sensitivity of the magnetic sensor.

DETAILED DESCRIPTION

Figure 1A:
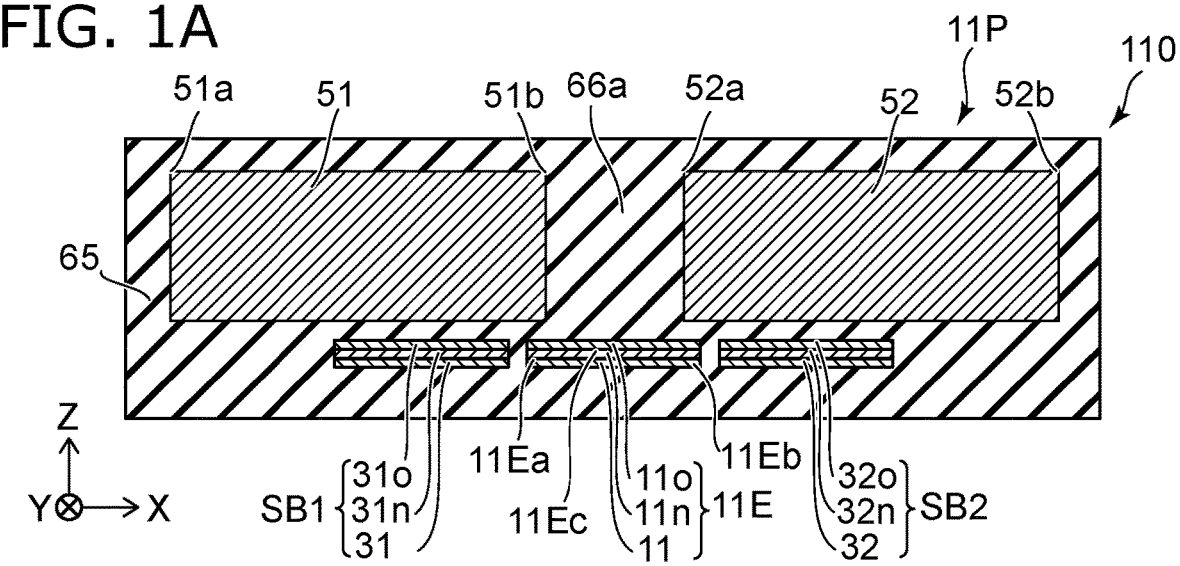
FIGS. 1A and 1B are schematic views illustrating a magnetic sensor according to a first embodiment.

According to one embodiment of the invention, a magnetic sensor includes a first element part. The first element part includes a first magnetic element, a first structure, a second structure, a first magnetic member, and a second magnetic member. The first magnetic element includes a first magnetic layer, a first counter magnetic layer, and a first nonmagnetic layer provided between the first magnetic layer and the first counter magnetic layer. A direction from the first magnetic layer toward the first counter magnetic layer is along a first direction. The first structure includes a first side magnetic layer. The second structure includes a second side magnetic layer. The first magnetic element is between the first structure and the second structure in a second direction crossing the first direction. The first magnetic element is separated from the first side magnetic layer and the second side magnetic layer. A direction from the first side magnetic layer toward the first magnetic member is along the first direction. A direction from the second side magnetic layer toward the second magnetic member is along the first direction. A direction from the first magnetic element toward a region between the first magnetic member and the second magnetic member is along the first direction.

According to one embodiment of the invention, an inspection device includes the above magnetic sensor, and a processor being configured to process a signal output from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
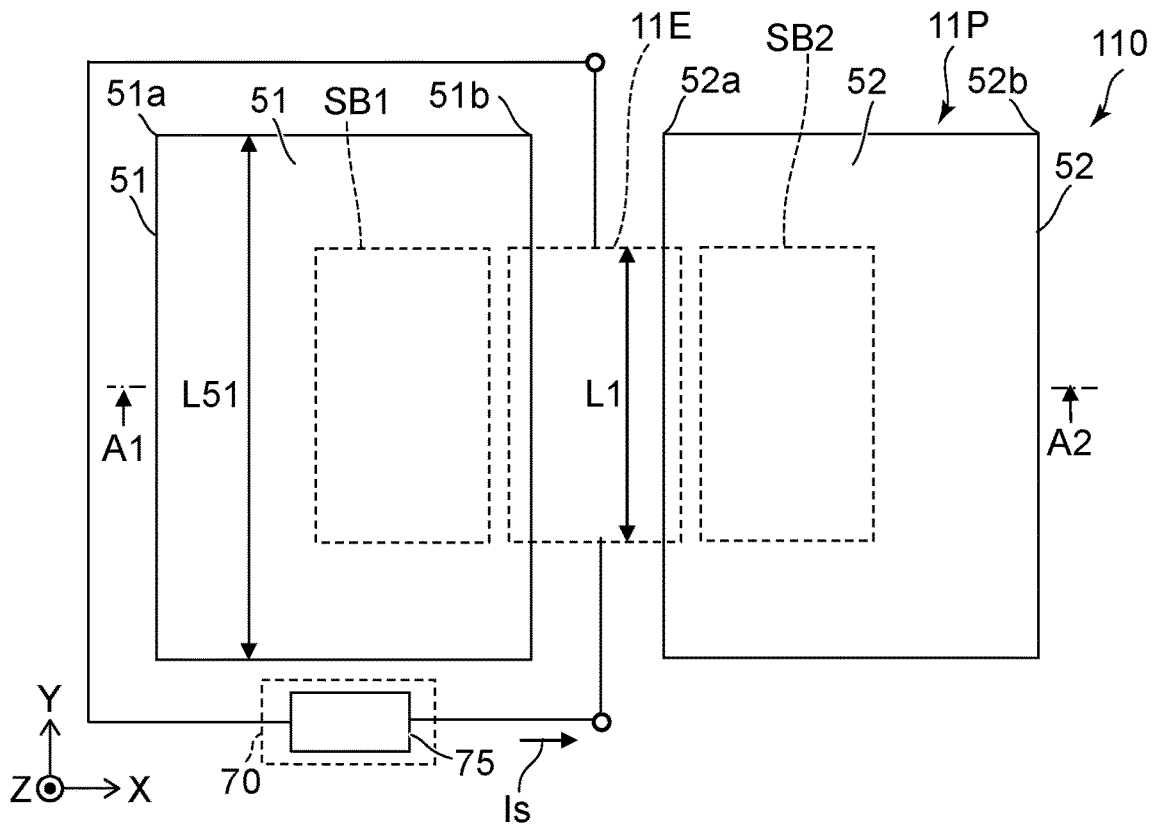

FIGS. 1A and 1B are schematic views illustrating a magnetic sensor according to a first embodiment.

FIG. 1A is a sectional view taken along line A1-A2 of FIG. 1B. FIG. 1B is a plan view. In these figures, some elements have been omitted to make the figures easier to read.

As shown in FIGS. 1A and 1B, a magnetic sensor 110 according to the embodiment includes a first element part 11P.

The first element part 11P includes a first magnetic element 11E, a first structure SB1, a second structure SB2, a first magnetic member 51, and a second magnetic member 52. The first magnetic element 11E includes a first magnetic layer 11, a first counter magnetic layer 11o, and a first non-magnetic layer 11n. The first non-magnetic layer 11n is provided between the first magnetic layer 11 and the first counter magnetic layer 11o. For example, the stacking order of the first magnetic layer 11 and the first counter magnetic layer 11o is arbitrary.

The direction from the first magnetic layer 11 to the first counter magnetic layer 11o is along the first direction. The first direction is the Z-axis direction. One direction perpendicular to the Z-axis direction is defined as the X-axis direction. The direction perpendicular to the Z-axis direction and the X-axis direction is defined as the Y-axis direction.

The first structure SB1 includes a first side magnetic layer 31. The second structure SB2 includes a second side magnetic layer 32. The first magnetic element 11E is between the first structure SB1 and the second structure SB2 in the second direction crossing the first direction. The second direction is, for example, the X-axis direction. The first magnetic element 11E is separated from the first side magnetic layer 31 and the second side magnetic layer 32. For example, the first magnetic element 11E is separated from the first structure SB1 and the second structure SB2.

The direction from the first magnetic element 11E to the region 66a between the first magnetic member 51 and the second magnetic member 52 is along the first direction (Z-axis direction). In this example, the insulating member 65 is provided. One region 66a of the insulating member 65 is between the first magnetic member 51 and the second magnetic member 52.

In this example, the first structure SB1 includes a first side counter magnetic layer 31o and a first side non-magnetic layer 31n. The direction from the first side magnetic layer 31 to the first side counter magnetic layer 31o is along the first direction (Z-axis direction). The first side non-magnetic layer 31n is between the first side magnetic layer 31 and the first side counter magnetic layer 31o.

In this example, the second structure SB2 includes a second side counter magnetic layer 32o and a second side non-magnetic layer 32n. The direction from the second side magnetic layer 32 to the second side counter magnetic layer 32o is along the first direction (Z-axis direction). The second side non-magnetic layer 32n is between the second side magnetic layer 32 and the second side counter magnetic layer 32o.

For example, the first magnetic layer 11 is between the first side magnetic layer 31 and the second side magnetic layer 32. For example, the first counter magnetic layer 11o is located between the first side counter magnetic layer 31o and the second side counter magnetic layer 32o. For example, the first non-magnetic layer 11n is between the first side non-magnetic layer 31n and the second side non-magnetic layer 32n.

For example, the materials of the first side magnetic layer 31 and the second side magnetic layer 32 are substantially the same as the materials of the first magnetic layer 11. For example, the materials of the first side counter magnetic layer 31o and the second side counter magnetic layer 32o are substantially the same as the materials of the first counter magnetic layer 11o. For example, the materials of the first side non-magnetic layer 31n and the second side non-magnetic layer 32n are substantially the same as the materials of the first non-magnetic layer 11n.

The above configuration in the magnetic sensor 110 can be formed, for example, by processing a stacked film to be the first magnetic element 11E, the first structure SB1 and the second structure SB2. At least one of the first magnetic layer 11 and the first counter magnetic layer 11o includes at least one of Fe, Ni and Co. The first non-magnetic layer 11n includes at least one selected from the group consisting of Cu, Ag and Au. The first magnetic element 11 is, for example, a GMR (Giant Magnetic Resistance) element.

As shown in FIG. 1B, the magnetic sensor 110 may be provided with the detection circuit 75. The detection circuit 75 may be included in, for example, the processor 70. The detection circuit 75 is configured to detect the electric resistance of the first magnetic element 11E. For example, the detection current Is is supplied from the detection circuit 75 to the first magnetic element 11E, and the detection circuit 75 is configured to output a signal corresponding to a change in an electric resistance of the first magnetic element 11E.

The electric resistance of the first magnetic element 11E changes according to a change in the magnetic field applied to the magnetic sensor 110. The magnetic field is a magnetic field to be detected and is an external magnetic field. The external magnetic field is introduced into the first magnetic element 11E via the first magnetic member 51 and the second magnetic member 52. The first magnetic member 51 and the second magnetic member 52 collect an external magnetic field. High detection sensitivity can be obtained by introducing the concentrated magnetic field into the first magnetic element 11E. The first magnetic member 51 and the second magnetic member 52 function as, for example, an MFC (Magnetic Flux Concentrator).

In the embodiment, in addition to the first magnetic element 11E, the first structure SB1 and the second structure SB2 are provided. As a result, higher sensitivity can be obtained as compared with the case where the first structure SB1 and the second structure SB2 are not provided. For example, higher sensitivity can be obtained as compared with the case where both ends of the first magnetic element 11E in the X-axis direction overlap with the first magnetic member 51 and the second magnetic member 52 in a large area. An example of the characteristics of the magnetic sensor will be described later.

As shown in FIG. 1A, the first magnetic element 11E includes a first magnetic element end portion 11Ea and a first magnetic element other end portion 11Eb. The first magnetic element end portion 11Ea is between the first structure SB1 and the first magnetic element other end portion 11Eb. The first magnetic element other end 11Eb is between the first magnetic element end portion 11Ea and the second structure SB2. The first magnetic member 51 includes a first magnetic member end portion 51a and a first magnetic member other end portion 51b. The second magnetic member 52 includes a second magnetic member end portion 52a and a second magnetic member other end portion 52b. In the second direction (for example, the X-axis direction), there is the first magnetic member other end 51b between the first magnetic member end portion 51a and the second magnetic member other end portion 52b. In the second direction, there is the second magnetic member end portion 52a between the first magnetic member other end portion 51b and the second magnetic member other end portion 52b.

In the example of FIG. 1A, the first magnetic element end portion 11Ea overlaps the first magnetic member 51 in the Z-axis direction. The first magnetic element other end portion 11Eb overlaps the second magnetic member 52 in the Z-axis direction. The first magnetic member other end portion 51b overlaps the first magnetic element 11E in the Z-axis direction. The second magnetic member end portion 52a overlaps the first magnetic element 11E in the Z-axis direction. The first magnetic element 11E includes a portion 11Ec between the first magnetic element end portion 11Ea and the first magnetic element other end portion 11Eb. The portion 11Ec corresponds to the central portion of the first magnetic element 11E in the second direction (for example, the X-axis direction). The portion 11Ec overlaps the region 66a in the Z-axis direction. As will be described later, the position of the end portion is deformable. The first magnetic member end portion 51a and the second magnetic member other end portion 52b may be inclined with respect to the Z-axis direction. The second magnetic member other end portion 52b may have, for example, a tapered side surface.

An example of the simulation result of the characteristics of the magnetic sensor will be described below.

Figure 2A:
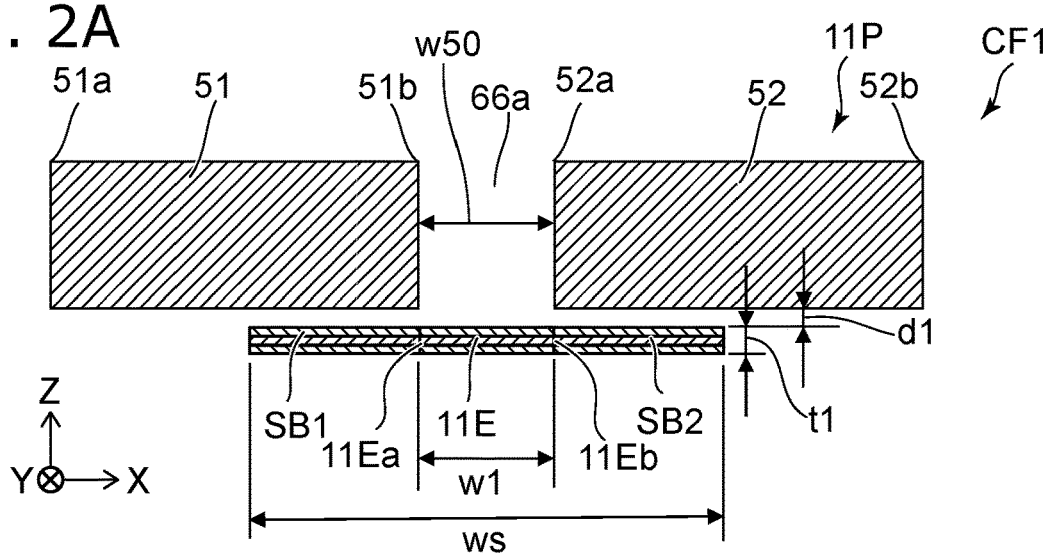
FIGS. 2A to 2C are schematic views illustrating a simulation model relating to the magnetic sensor.
Figure 2B:
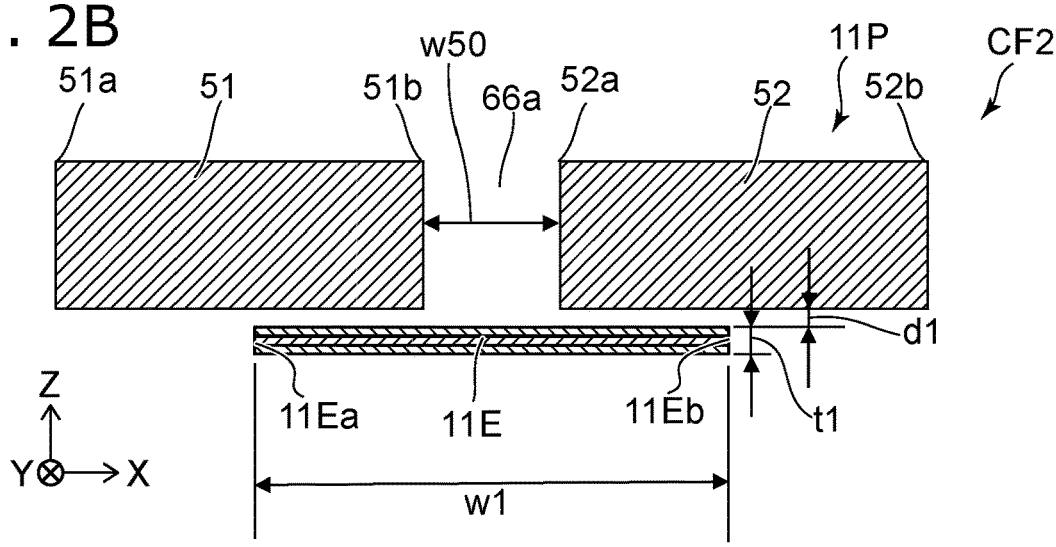
Figure 2C:
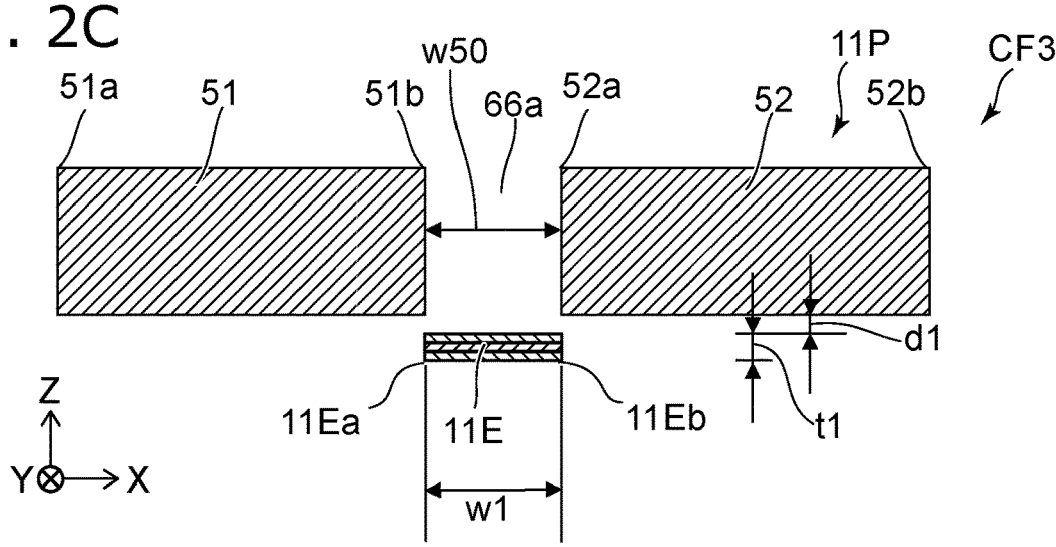

FIGS. 2A to 2C are schematic views illustrating a simulation model relating to a magnetic sensor.

As shown in FIG. 2A, in the first configuration CF1 which is a simulation model, the first magnetic element 11E, the first structure SB1 and the second structure SB2 are provided. In the simulation model, the first magnetic element 11E is in contact with the first structure SB1 and the second structure SB2. However, the first magnetic element 11E is electrically insulated from the first structure SB1 and the second structure SB2. In the first configuration CF1, the total width ws of the first magnetic element 11E, the first structure SB1 and the first structure SB2 in the X-axis direction is constant at 8 μm. The first magnetic element end portion 11Ea overlaps the first magnetic member other end portion 51b in the Z-axis direction. The first magnetic element other end portion 11Eb overlaps the second magnetic member end portion 52a in the Z-axis direction. The width w1 of the first magnetic element 11E in the X-axis direction is the same as the distance (gap length w50) between the first magnetic member 51 and the second magnetic member 52. The average magnetic flux density in the first magnetic element 11E when the gap length w50 (that is, the width w1) is changed by 1 μm to 7 μm is calculated by simulation. In the simulation, the distance dl between the first magnetic element 11E and the first magnetic member 51 is 0.3 μm. The thickness t1 (length along the Z-axis direction) of the first magnetic element 11E is 0.03 μm. The length L1 of the first magnetic element 11E along the Y-axis direction (see FIG. 1B) is 500 μm. The length L51 (see FIG. 1B) of the first magnetic member 51 along the Y-axis direction is 100 μm.

As shown in FIGS. 2B and 2C, in the second configuration CF2 and the third configuration CF3, which are simulation models, the first magnetic element 11E is provided, and the first structure SB1 and the second structure SB2 are not provided. In the second configuration CF2, the width w1 of the first magnetic element 11E in the X-axis direction is constant at 8 μm. In the second configuration CF2, the average magnetic flux density in the first magnetic element 11E when the gap length w50 is changed from 1 μm to 7 μm is calculated by simulation. In the third configuration CF3, the width w1 of the first magnetic element 11E in the X-axis direction is the same as the gap length w50. In the third configuration CF3, the average magnetic flux density in the first magnetic element 11E when the gap length w50 is changed from 1 μm to 7 μm is calculated by simulation.

In the simulations of the first to third configurations CF1 to CF3, the average magnetic flux density in the first magnetic element 11E when the magnetic field of 10e is applied as the external magnetic field is calculated.

Figure 3:
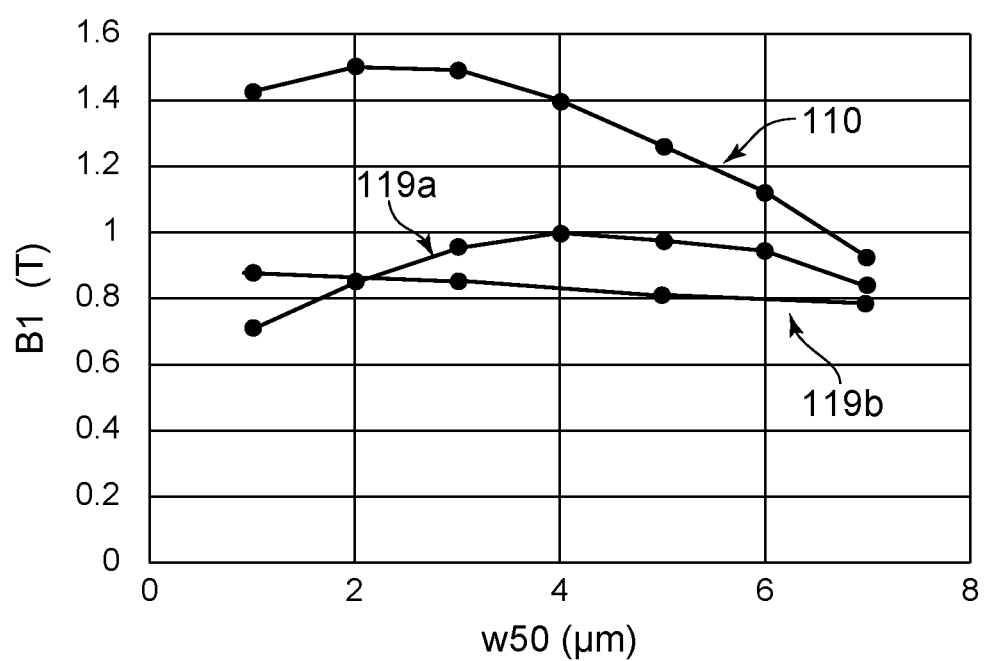
FIG. 3 is a graph illustrating the characteristics of the magnetic sensor.

FIG. 3 is a graph illustrating the characteristics of the magnetic sensor.

The horizontal axis of FIG. 3 is the gap length w50 (μm). The vertical axis is the average magnetic flux density B1 (T) in the first magnetic element 11E. As shown in FIG. 3, in the first configuration CF1, the average magnetic flux density B1 in the first magnetic element 11E is higher than that in the second configuration CF2 and the third configuration CF3.

In the region overlapping the first magnetic member 51 or the second magnetic member 52, which is separated from the region 66a between the first magnetic member 51 and the second magnetic member 52 along the X-axis direction, the detected magnetic field mainly passes through the first magnetic member 51 and the second magnetic member 52. In this portion, it is considered that the detected magnetic field is weaker than that of the region 66a. In the second configuration CF2, the area of the region where the magnetic field is weak in the first magnetic element 11E is large. Therefore, the average magnetic flux density B1 in the first magnetic element 11E is low. In the second configuration CF2, the rate of change of the electric resistance in the first magnetic element 11E with respect to the change of the external magnetic field is low. Therefore, it is difficult to increase the sensitivity sufficiently.

In the third configuration CF3, the first magnetic element 11E is provided corresponding to the region 66a between the first magnetic member 51 and the second magnetic member 52. Therefore, there is no significant difference in the average magnetic flux density B1 between the second configuration CF2 and the third configuration CF3. In the third configuration CF3, the width (length along the X-axis direction) of the first magnetic element 11E is smaller than that of the second configuration CF2. Therefore, the demagnetic field becomes large, and the detected magnetic flux does not easily enter the first magnetic element 11E. However, in the third configuration CF3, the magnetic flux of the first magnetic element 11E is unlikely to decrease in the region overlapping the first magnetic member 51 or the second magnetic member 52. As a result, it is considered that there is no significant difference in the average magnetic flux density B1 between the second configuration CF2 and the third configuration CF3.

In the first configuration CF1, the average magnetic flux density B1 in the first magnetic element 11E is higher than the average magnetic flux density B1 in the second configuration CF2 and the third configuration CF3. In the first configuration CF1, no current flows through the first structure SB1 and the second structure SB2. Therefore, in the first structure SB1 and the second structure SB2, the decrease in sensitivity due to the decrease in magnetic flux density is suppressed. Further, for example, by sufficiently reducing the distance between the first structure SB1 and the first magnetic element 11E and the distance between the second structure SB2 and the first magnetic element 11E, due to the effects of the first structure SB1 and the second structure SB2, the demagnetic field in the first magnetic element 11E becomes smaller as in the second configuration CF2. In the first configuration CF1, the first magnetic element 11E is provided corresponding to the region 66a between the first magnetic member 51 and the second magnetic member 52, and further, the first structure SB1 and the second structure SB2 is provided. As a result, it is considered that a larger amount of magnetic field can be introduced into the first magnetic element 11E. High sensitivity can be obtained in the first configuration CF1.

Hereinafter, some examples of the magnetic sensor according to the embodiment will be described.

Figure 4A:
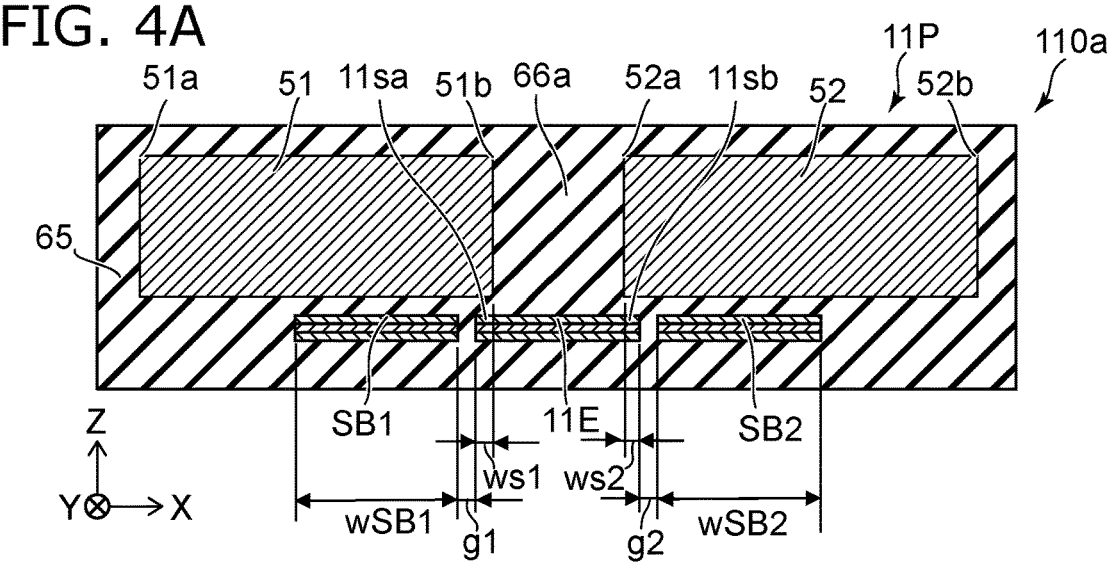
FIGS. 4A to 4C are schematic cross-sectional views illustrating the magnetic sensor according to the first embodiment.
Figure 4B:
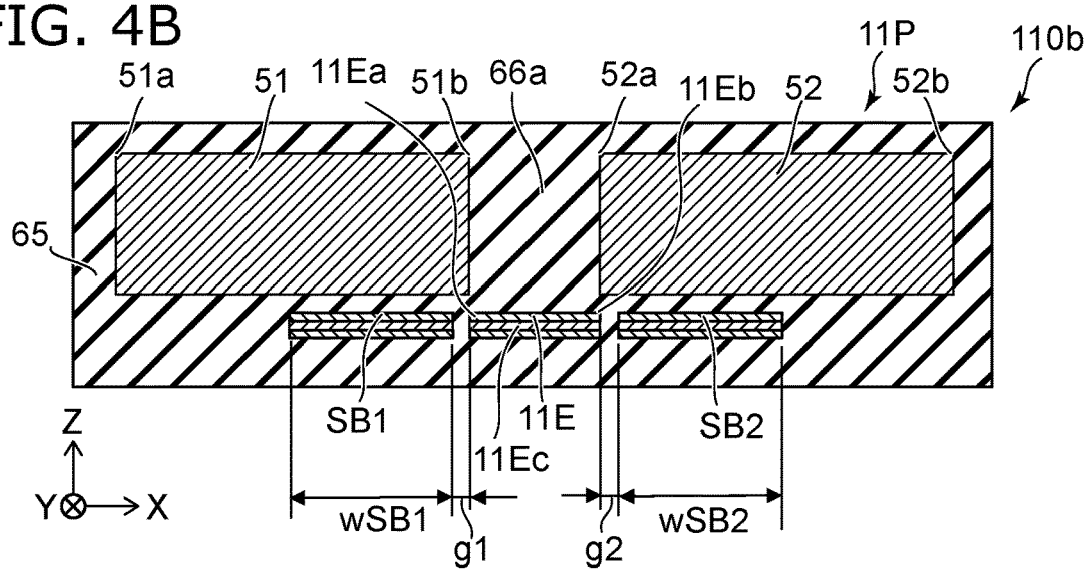
Figure 4C:
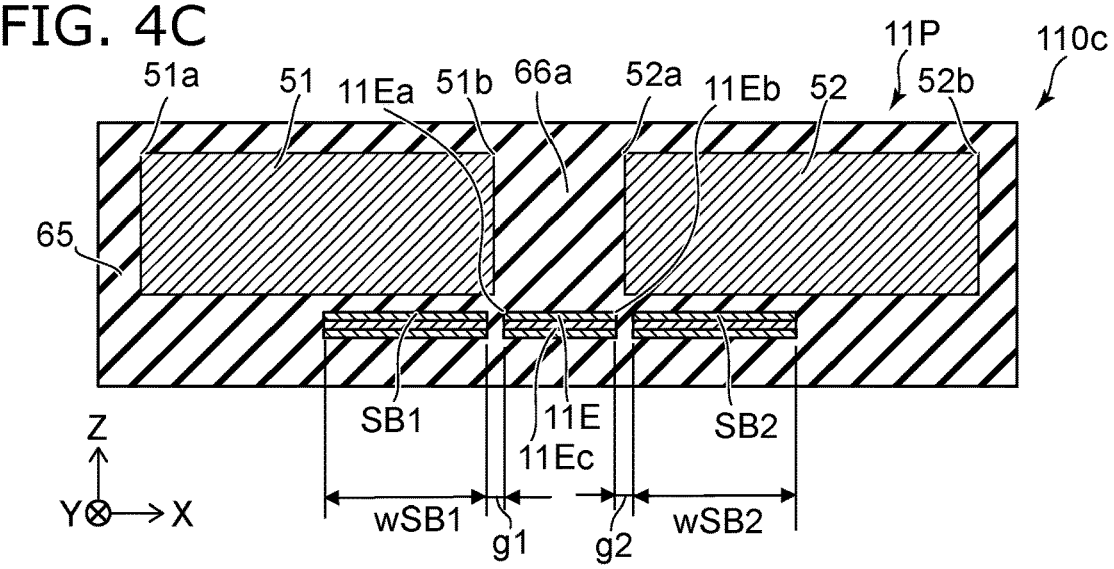

FIGS. 4A to 4C are schematic cross-sectional views illustrating the magnetic sensor according to the first embodiment.

As shown in FIG. 4A, in the magnetic sensor 110a, both ends of the first magnetic element 11E overlap the first magnetic member 51 and the second magnetic member 52.

For example, the first magnetic element 11E includes a first superimposition region 11sa and a second superimposition region 11sb. The first superimposition region 11sa overlaps the first magnetic member 51 in the first direction (Z-axis direction). The second superimposition region 11sb overlaps the second magnetic member 52 in the first direction. The width (length) of these superimposition regions along the X-axis direction is small. For example, the length ws1 along the second direction (for example, the X-axis direction) of the first superimposition region 11sa is shorter than the length wSB1 along the second direction of the first structure SB1. The length ws2 of the second superimposition region 11sb along the second direction is shorter than the length wSB2 of the second structure SB2 along the second direction. Since the width (length) of the superposed region along the X-axis direction is small, a high magnetic field can be effectively introduced into the first magnetic element 11E. In one example, for example, the length ws1 is 0.01 times or more and 0.9 times or less the length wSB1. For example, the length ws2 is 0.01 times or more and 0.9 times or less the length wSB2.

As shown in FIG. 4B, in the magnetic sensor 110b, both ends of the first magnetic element 11E overlap the inner end of the first magnetic member 51 and the inner end of the second magnetic member 52. For example, the first magnetic element end portion 11Ea overlaps the first magnetic member other end portion 51b of in the first direction (Z-axis direction). The first magnetic element other end portion 11Eb overlaps the second magnetic member end portion 52a in the first direction. The first magnetic element 11E is provided corresponding to the region 66a between the first magnetic member 51 and the second magnetic member 52, which have a high magnetic field strength. Further, the first structure SB1 and the second structure SB2 are provided. As a result, high sensitivity can be obtained.

As shown in FIG. 4C, in the magnetic sensor 110c, both ends of the first magnetic element 11E are inside the first magnetic member 51 and the second magnetic member 52. For example, the position of the first magnetic element end portion 11Ea in the second direction (for example, the X-axis direction) is between the position of the first magnetic member other end portion 51b in the second direction and the position of the second magnetic member end portion 51a in the second direction. The position of the first magnetic element other end portion 11Eb in the second direction is between the position of the first magnetic member other end portion 51b in the second direction and the position of the second magnetic member end portion 52a in the second direction. The first magnetic element 11E is provided corresponding to the region 66a between the first magnetic member 51 and the second magnetic member 52, which have a high magnetic field strength. Further, the first structure SB1 and the second structure SB2 are provided. As a result, high sensitivity can be obtained.

In the embodiment, one of the first magnetic element end portion 11Ea and the first magnetic element other end portion 11Eb may overlap the first magnetic member 51 or the second magnetic member 52 in the Z-axis direction.

As shown in FIG. 4A, for example, in the embodiment, the distance between the first magnetic layer 11 and the first side magnetic layer 31 along the second direction (for example, the X-axis direction) is defined as a distance g1. In the embodiment, the distance g1 is preferably 0.5 nm or more, for example. The distance g1 is preferably, for example, a thickness t1 (see FIG. 2A) or less of the first magnetic element 11E. The distance between the first magnetic layer 11 and the first side counter magnetic layer 32o along the second direction is defined as a distance g2. The distance g2 is preferably 0.5 nm or more, for example. The distance g2 is preferably, for example, the thickness t1 (see FIG. 2A) or less of the first magnetic element 11E. When these distances are 0.5 nm or more, good insulating properties can be obtained. When these distances are t1 or less in thickness, it becomes easy to obtain a magnetic coupling between the first magnetic element 11E and the magnetic member. For example, the demagnetic field in the first magnetic element 11E can be reduced. For example, it becomes easier to introduce an external magnetic field into the first magnetic element 11E more efficiently.

In the embodiment, the length of the first magnetic element 11E in the third direction is defined as a length L1 (FIG. 1B). The third direction crosses the plane including the first direction and the second direction. The third direction is, for example, along the Y-axis direction. In one example, the length L1 (see FIG. 1B) is longer than the width w1 (see FIG. 2A). For example, the length of the first magnetic layer 11 along the Y-axis direction is longer than the length of the first magnetic layer 11 along the X-axis direction. For example, the length of the first counter magnetic layer 11o along the Y-axis direction is longer than the length of the first counter magnetic layer 11o along the X-axis direction. For example, the length of the first non-magnetic layer 11n along the Y-axis direction is longer than the length of the first non-magnetic layer 11n along the X-axis direction. In one example, in the absence of an external magnetic field, the magnetization of the first magnetic layer 11 is along the Y-axis direction and the magnetization of the first counter magnetic layer 11o is along the Y-axis direction.

In one example, one of the first magnetic layer 11 and the first counter magnetic layer 11o is a magnetization free layer, and the other of the first magnetic layer 11 and the first counter magnetic layer 11o is a reference layer. In another example, both the first magnetic layer 11 and the first counter magnetic layer 11o may be magnetized free layers. At least one of the magnetization direction of the first magnetic layer 11 and the magnetization direction of the first counter magnetic layer 11o changes according to the change of the external magnetic field. The electric resistance of the first magnetic element 11E changes according to the change in the direction of magnetization.

Figure 5A:
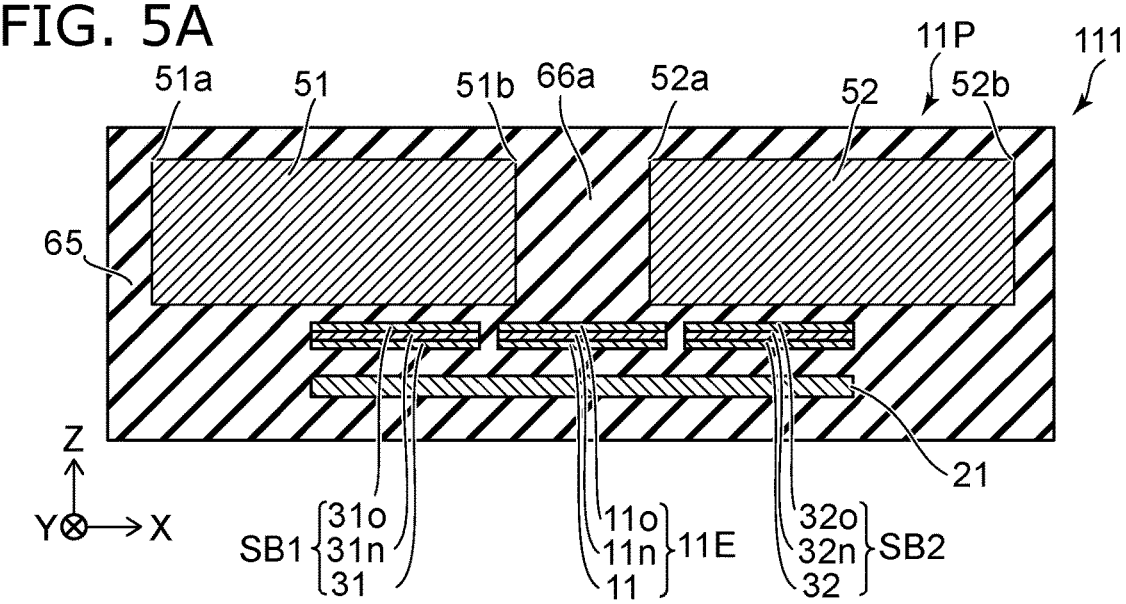
FIGS. 5A and 5B are schematic views illustrating the magnetic sensor according to the first embodiment.
Figure 5B:
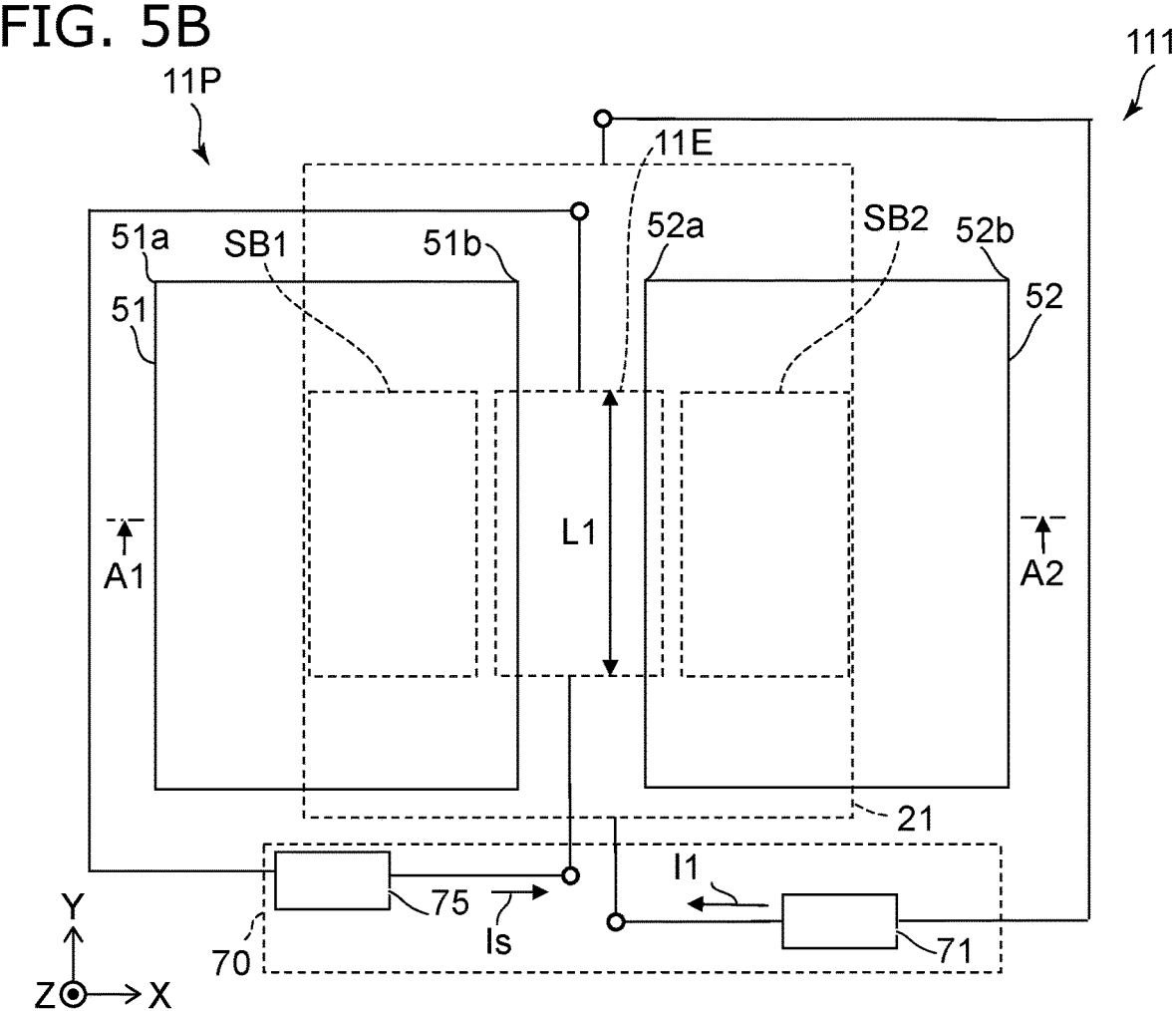

FIGS. 5A and 5B are schematic views illustrating the magnetic sensor according to the first embodiment.

FIG. 5A is a sectional view taken along line A1-A2 of FIG. 5B. FIG. 5B is a plan view. In these figures, some elements have been omitted to make the figures easier to read.

As shown in FIGS. 5A and 5B, the magnetic sensor 111 according to the embodiment includes the first element part 11P. In the magnetic sensor 111, the first element part 11P includes a first conductive member 21 in addition to the first magnetic element 11E, the first structure SB1, the second structure SB2, the first magnetic member 51, and the second magnetic member 52. In the magnetic sensor 111, the configurations of the first magnetic element 11E, the first structure SB1, the second structure SB2, the first magnetic member 51, and the second magnetic member 52 may be the same as those of the magnetic sensor 110 or the magnetic sensors 110a to 110c.

As shown in FIG. 5A, the first conductive member 21 overlaps the first magnetic element 11E in the first direction (Z-axis direction).

As shown in FIG. 5B, the first conductive member 21 can be supplied with a first current I1 including an AC component. For example, the first circuit 71 is provided. The first circuit 71 may be included in the processor 70. The first current I1 is supplied from the first circuit 71 to the first conductive member 21. The first current I1 flows along the Y-axis direction. The first current I1 creates a magnetic field having a component in the Z-axis direction. This magnetic field is applied to the first magnetic element 11E. For example, the magnetic field due to the first current I1 is also collected by the first magnetic member 51 and the second magnetic member 52, and the concentrated magnetic field is introduced into the first magnetic element 11E.

Hereinafter, an example of a change in the electric resistance of the first magnetic element 11E when a current flows through the first conductive member 21 will be described.

Figure 6A:
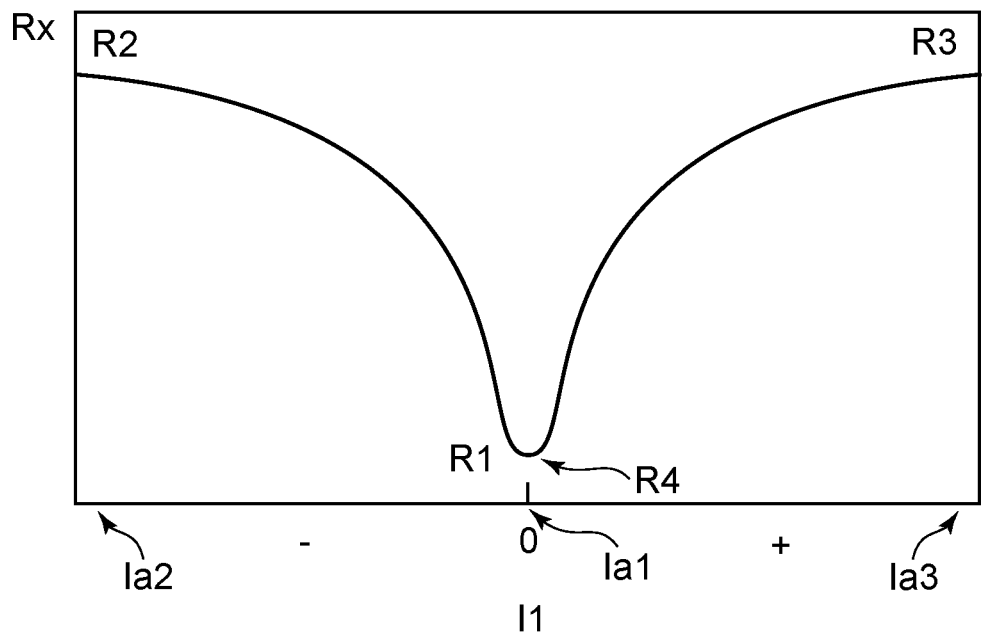
FIGS. 6A and 6B are schematic views illustrating the characteristics of the magnetic sensor according to the first embodiment.
Figure 6B:
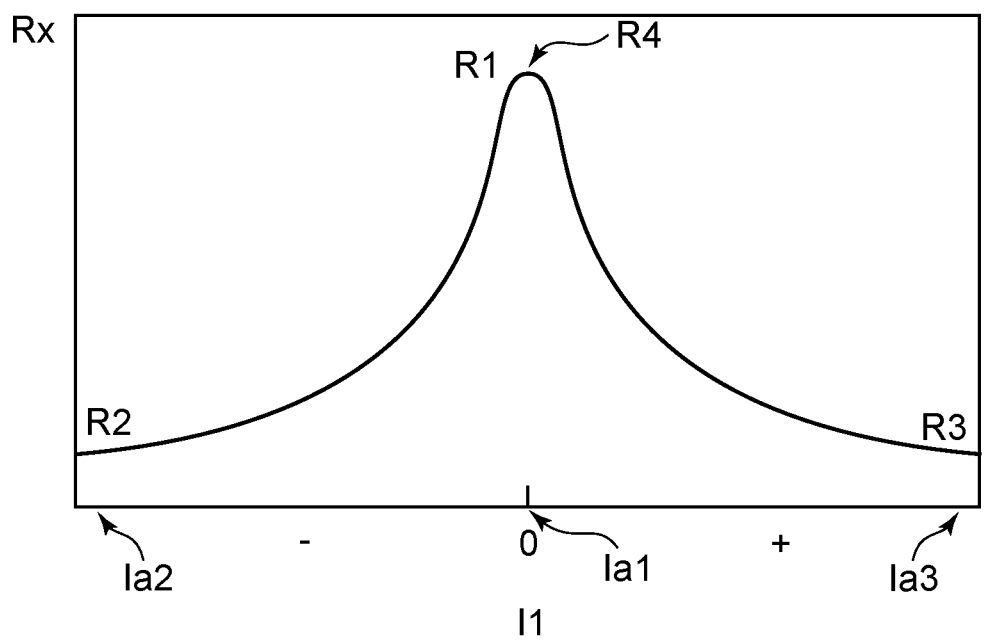

FIGS. 6A and 6B are schematic views illustrating the characteristics of the magnetic sensor according to the first embodiment.

The horizontal axis of these figures corresponds to the value of the current (for example, the first current I1) flowing through the first conductive member 21. The vertical axis is the electric resistance Rx of the first magnetic element 11E. As shown in FIGS. 6A and 6B, in the embodiment, the electric resistance Rx shows the characteristic of an even function with respect to the change of the current (first current I1).

For example, the electric resistance Rx of the first magnetic element 11E has a first value R1 when the first value current Ia1 is supplied to the first conductive member 21. The electric resistance Rx has a second value R2 when the second value current Ia2 is supplied to the first conductive member 21. The electric resistance Rx has a third value R3 when the third value current Ia3 is supplied to the first conductive member 21. The absolute value of the first value current Ia1 is smaller than the absolute value of the second value current Ia2 and smaller than the absolute value of the third value current Ia3. The first value current Ia1 may be, for example, substantially 0. The direction of the second value current Ia2 is opposite to the direction of the third value current Ia3.

In the example of FIG. 6A, the first value R1 is lower than the second value R2 and lower than the third value R3. In the example of FIG. 6A, the electric resistance Rx has a "valley-shaped" characteristic. The first value R1 is, for example, the lowest value of electric resistance. In the example of FIG. 6B, the first value R1 is higher than the second value R2 and higher than the third value R3. In the example of FIG. 6B, the electric resistance Rx has a "mountain-shaped" characteristic. The first value R1 is, for example, the maximum value of electric resistance.

For example, when the external magnetic field is substantially 0, the magnetization of the first magnetic layer 11 and the magnetization of the first counter magnetic layer 11o are in a "parallel arrangement", and for example, when interlayer magnetic coupling acts, "Valley-shaped" characteristics are obtained. At this time, for example, the thickness of the first non-magnetic layer 11n is 2.5 nm or more. For example, when the external magnetic field is substantially 0, the magnetization of the first magnetic layer 11 and the magnetization of the first counter magnetic layer 11o are in an "antiparallel arrangement", and for example, when interlayer magnetic coupling acts, "mountain shaped" characteristics are obtained. In this case, the thickness of the first non-magnetic layer 11n is, for example, 1.9 nm or more and 2.1 nm or less.

For example, when no current flows through the first conductive member 21, the electric resistance Rx has a fourth value R4. For example, the first value R1 is substantially the same as the fourth value R4 when no current flows.

For example, the ratio of the absolute value of the difference between the first value R1 and the fourth value R4 to the fourth value R4 is 0.01 or less. The ratio may be 0.001 or less. For positive and negative currents, the characteristics of an even function are obtained.

The relationship between the first current I1 and the electric resistance Rx is based on such that the magnetic field due to the first current I1 is applied to the first magnetic element 11E, and the electric resistance Rx of the first magnetic element 11E changes depending on the strength of the magnetic field.

The electric resistance Rx when an external magnetic field is applied to the first magnetic element 11E also shows the characteristics of an even function as in the example shown in FIG. 6A or FIG. 6B. The external magnetic field includes, for example, components along the X-axis direction.

Figure 7A:
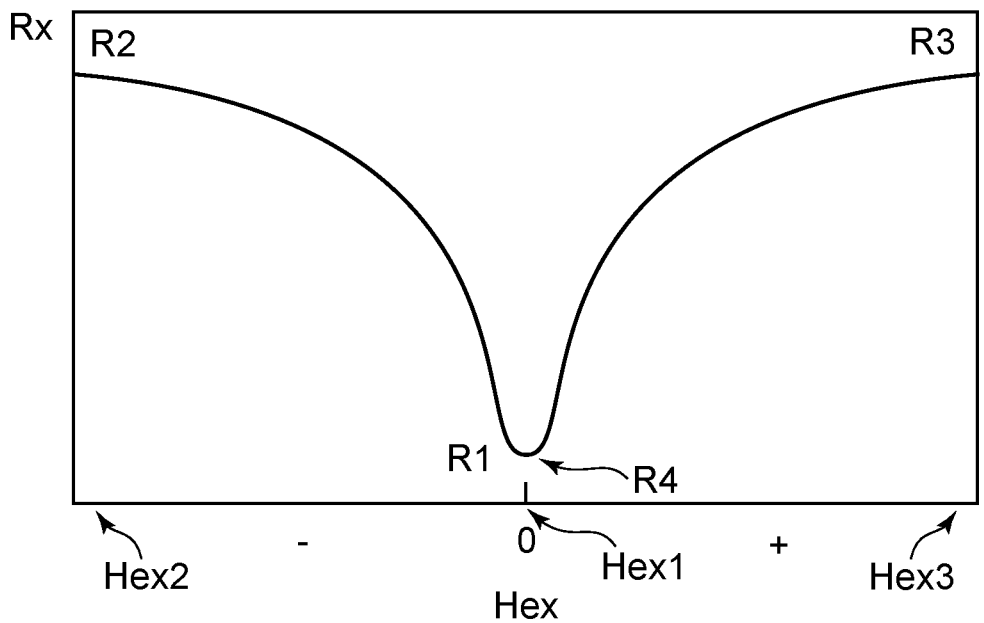
FIGS. 7A and 7B are schematic views illustrating the characteristics of the magnetic sensor according to the first embodiment.
Figure 7B:
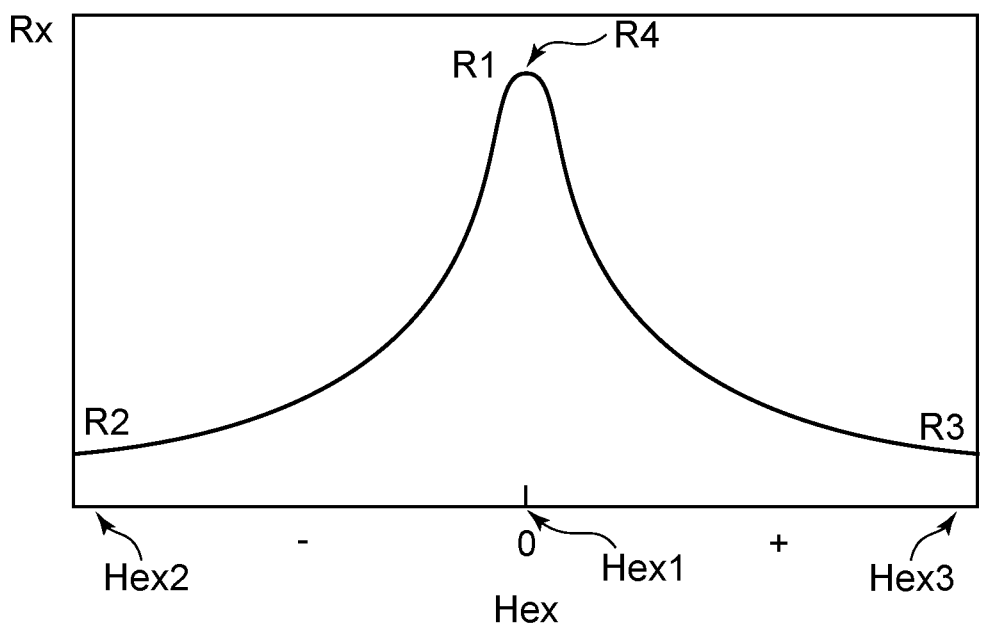

FIGS. 7A and 7B are schematic views illustrating the characteristics of the magnetic sensor according to the first embodiment.

The horizontal axis in these figures is the intensity of the external magnetic field Hex applied to the first magnetic element 11E. The vertical axis is the electric resistance Rx of the first magnetic element 11E. These figures correspond to the RH characteristics. As shown in FIGS. 7 (a) and 7 (b), the electric resistance Rx has characteristics of an even function with respect to the magnetic field (external magnetic field Hex, for example, the magnetic field in the X-axis direction) applied to the first magnetic element 11E.

As shown in FIGS. 7A and 7B, the electric resistance Rx of the first magnetic element 11E has a first value R1 when the first magnetic field Hex1 is applied to the first magnetic element 11E. The electric resistance Rx has a second value R2 when a second magnetic field Hex2 is applied to the first magnetic element 11E. The electric resistance Rx has a third value R3 when a third magnetic field Hex3 is applied to the first magnetic element 11E. The absolute value of the first magnetic field Hex1 is smaller than the absolute value of the second magnetic field Hex2 and smaller than the absolute value of the third magnetic field He3. The direction of the second magnetic field Hex2 is opposite to the direction of the third magnetic field Hex3.

In the example of FIG. 7A, the first value R1 is lower than the second value R2 and lower than the third value R3. In the example of FIG. 8B, the first value R1 is higher than the second value R2 and higher than the third value R3. For example, when no external magnetic field is applied to the first magnetic element 11E, the electric resistance Rx has a fourth value R4. The first value R1 is substantially the same as the fourth value R4 when no external magnetic field is applied. For example, the ratio of the absolute value of the difference between the first value R1 and the fourth value R4 to the fourth value R4 is 0.01 or less. The ratio may be 0.001 or less. The characteristics of even functions are obtained with respect to positive and negative external magnetic fields.

Utilizing the characteristics of such even functions, high-sensitivity detection is possible as follows.

In the following, an example will be described in which the first current I1 is an alternating current and does not substantially include a direct current component. A first current I1 (alternating current) is supplied to the first conductive member 21, and an alternating magnetic field generated by the alternating current is applied to the first magnetic element 11E. An example of the change in the electric resistance Rx at this time will be described.

Figure 8A:
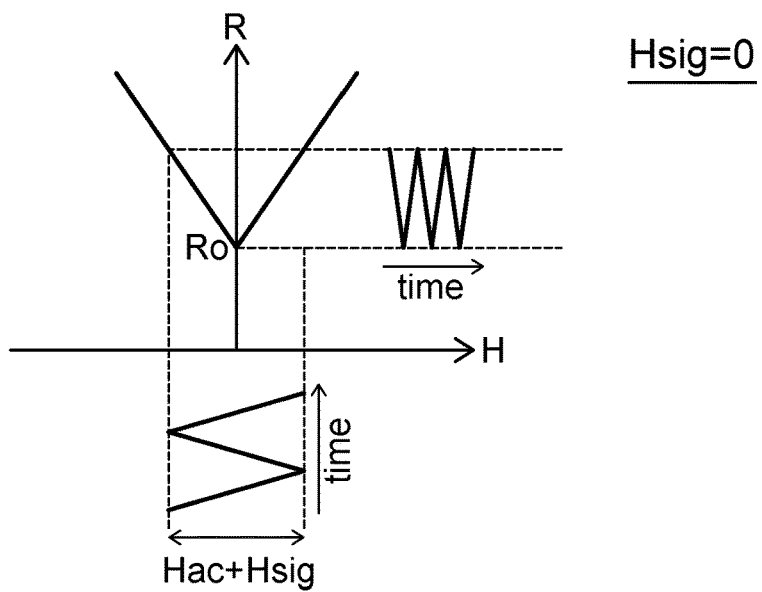
FIGS. 8A to 8C are graphs illustrating the characteristics of the magnetic sensor according to the first embodiment.
Figure 8B:
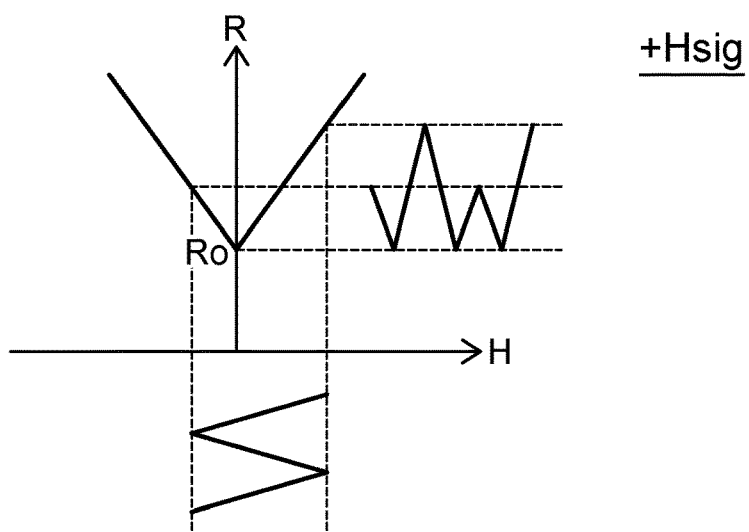
Figure 8C:
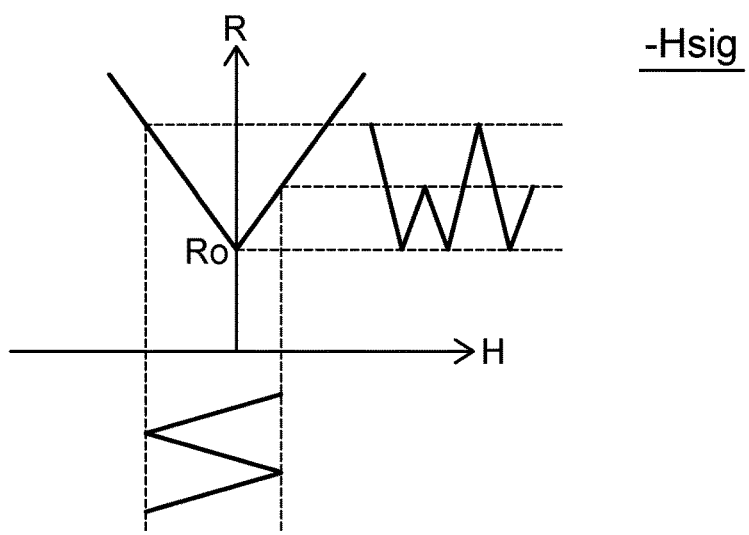

FIGS. 8A to 8C are graphs illustrating the characteristics of the magnetic sensor according to the first embodiment.

FIG. 8A shows the characteristics when the signal magnetic field Hsig (external magnetic field) applied to the first magnetic element 11E is 0. FIG. 8B shows the characteristics when the signal magnetic field Hsig is positive. FIG. 8C shows the characteristics when the signal magnetic field Hsig is negative. These figures show the relationship between the magnetic field H and the resistance R (corresponding to the electric resistance Rx).

As shown in FIG. 8A, when the signal magnetic field Hsig is 0, the resistor R exhibits a characteristic symmetric with respect to the positive and negative magnetic fields H. When the alternating magnetic field Hac is zero, the resistance R is a low resistance Ro. For example, the magnetization of the magnetization free layer rotates in substantially the same manner with respect to the positive and negative magnetic fields H. Therefore, a symmetrical change in resistance can be obtained. The fluctuation of the resistance R with respect to the alternating magnetic field Hac has the same value with positive and negative polarities. The period of change of the resistance R is ½ times the period of the alternating magnetic field Hac. The change in resistance R has substantially no frequency component of the alternating magnetic field Hac.

As shown in FIG. 8B, when a positive signal magnetic field Hsig is applied, the characteristic of the resistor R shifts to the side of the positive magnetic field H. In the alternating magnetic field Hac on the positive side, for example, the resistance R becomes high. In the alternating magnetic field Hac on the negative side, the resistance R becomes small.

As shown in FIG. 8C, when a negative signal magnetic field Hsig is applied, the characteristic of the resistor R shifts to the side of the negative magnetic field H. In the alternating magnetic field Hac on the positive side, for example, the resistance R becomes low. In the alternating magnetic field Hac on the negative side, the resistance R becomes large.

When a signal magnetic field Hsig of a predetermined magnitude is applied, the resistance R fluctuates differently with respect to the positive and negative of the alternating magnetic field Hac. The period of fluctuation of the resistance R with respect to the positive and negative of the alternating magnetic field Hac is the same as the period of the alternating magnetic field Hac. The output voltage of the AC frequency component corresponding to the signal magnetic field Hsig is generated.

The above characteristics are obtained when the signal magnetic field Hsig does not change with time. When the signal magnetic field Hsig changes with time, it becomes as follows. The frequency of the signal magnetic field Hsig is defined as the signal frequency fsig. Let the frequency of the alternating magnetic field Hac be the AC frequency fac. At this time, an output corresponding to the signal magnetic field Hsig is generated at a frequency of fac±fsig.

When the signal magnetic field Hsig changes with time, the signal frequency fsig is, for example, 1 kHz or less. On the other hand, the AC frequency fac is sufficiently higher than the signal frequency fsig. For example, the AC frequency fac is 10 times or more the signal frequency fsig.

For example, the signal magnetic field Hsig can be detected with high accuracy by extracting the output voltage of a component (AC frequency component) having the same period (frequency) as the period (frequency) of the alternating magnetic field Hac. In the magnetic sensor 111 according to the embodiment, it is possible to detect the external magnetic field Hex (signal magnetic field Hsig) to be detected with high sensitivity by utilizing such characteristics. In the embodiment, the first magnetic member 51 and the second magnetic member 52 can efficiently apply the external magnetic field Hex (signal magnetic field Hsig) and the alternating magnetic field Hac due to the first current I1 to the first magnetic element 11E. High sensitivity is obtained.

Figure 9A:
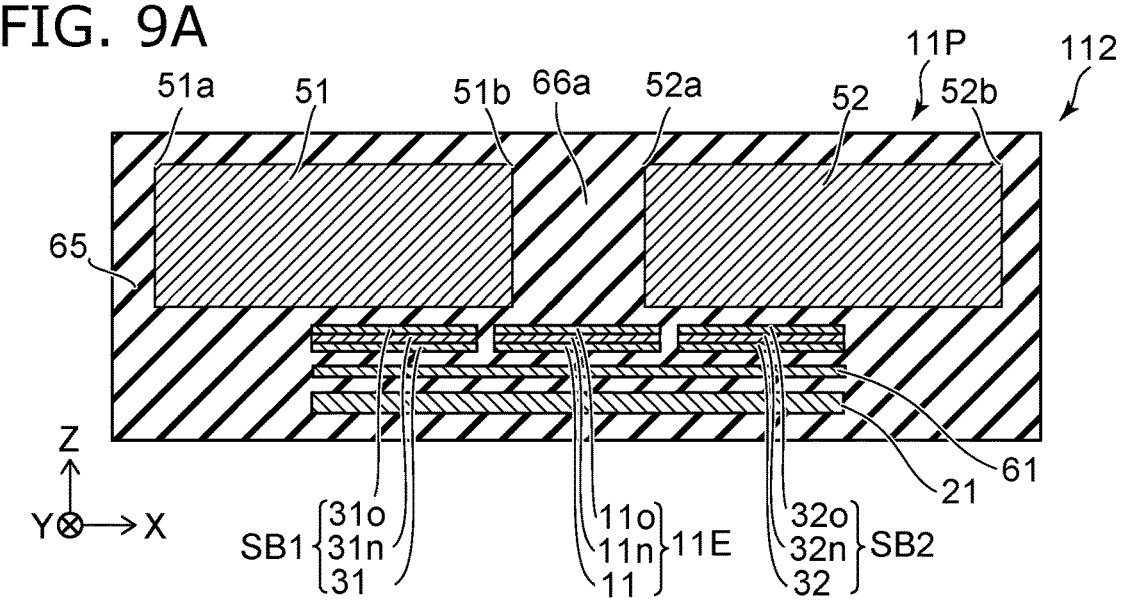
FIGS. 9A and 9B are schematic views illustrating the magnetic sensor according to the first embodiment.
Figure 9B:
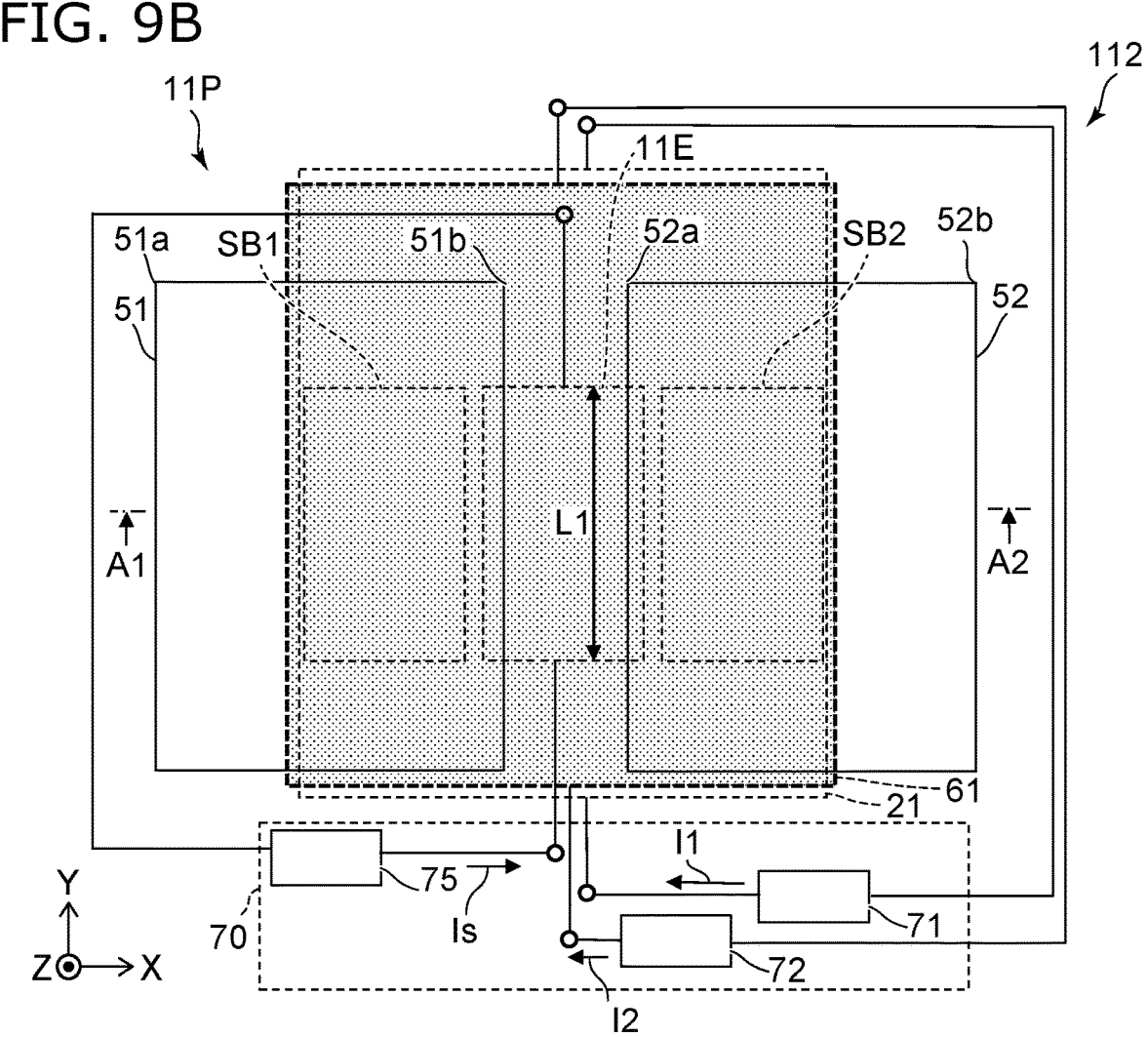

FIGS. 9A and 9B are schematic views illustrating the magnetic sensor according to the first embodiment.

FIG. 9A is a cross-sectional view taken along line A1-A2 of FIG. 9B. FIG. 9B is a plan view. In these figures, some elements have been omitted to make the figures easier to read.

As shown in FIGS. 9A and 9B, the magnetic sensor 112 according to the embodiment includes the first element part 11P. In the magnetic sensor 112, the first element part 11P includes a first conductive portion 61 in addition to the first magnetic element 11E, the first structure SB1, the second structure SB2, the first magnetic member 51, and the second magnetic member 52. In this example, the magnetic sensor 112 includes the first conductive member 21. In the magnetic sensor 112, the configurations of the first magnetic element 11E, the first structure SB1, the second structure SB2, the first magnetic member 51, and the second magnetic member 52 may be the same as those of the magnetic sensor 110 or 110a to 110c.

The first conductive portion 61 overlaps the first magnetic element 11E in the first direction (Z-axis direction). As shown in FIG. 9B, for example, a second circuit 72 is provided. The second circuit 72 is configured to supply a second current I2 (for example, a direct current) to the first conductive portion 61. The influence of noise (for example, geomagnetism) on the first magnetic element 11E can be suppressed by the current supplied to the first conductive portion 61. Higher accuracy detection is possible.

In this example, the first conductive portion 61 is provided between the first conductive member 21 and the first magnetic element 11E. The first conductive member 21 may be provided between the first conductive portion 61 and the first magnetic element 11E.

Second Embodiment

Figure 10A:
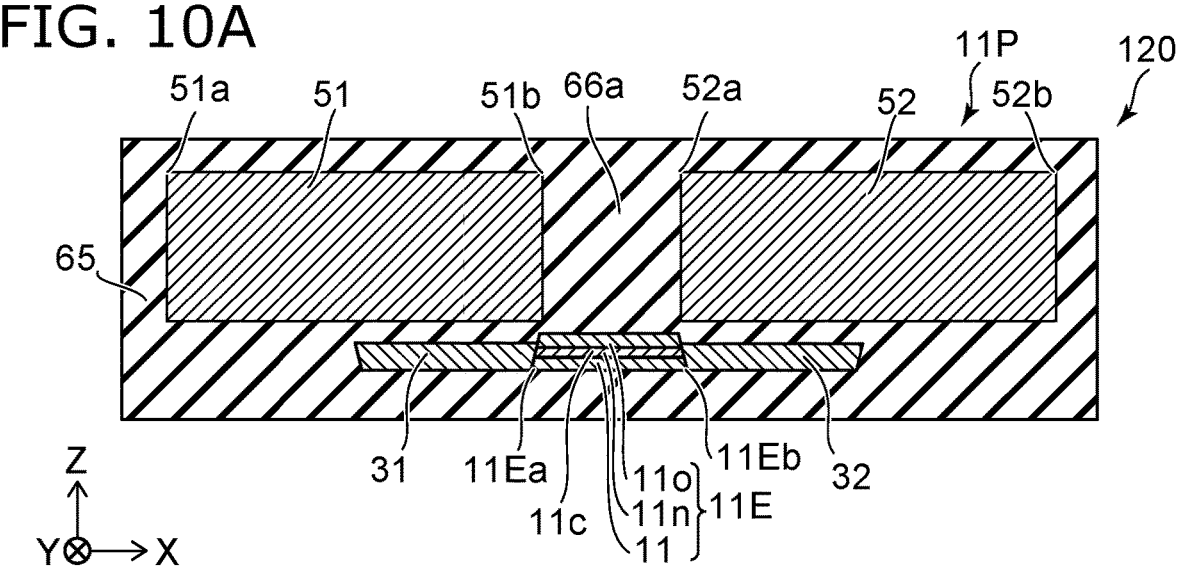
FIGS. 10A and 10B are schematic views illustrating a magnetic sensor according to a second embodiment.
Figure 10B:
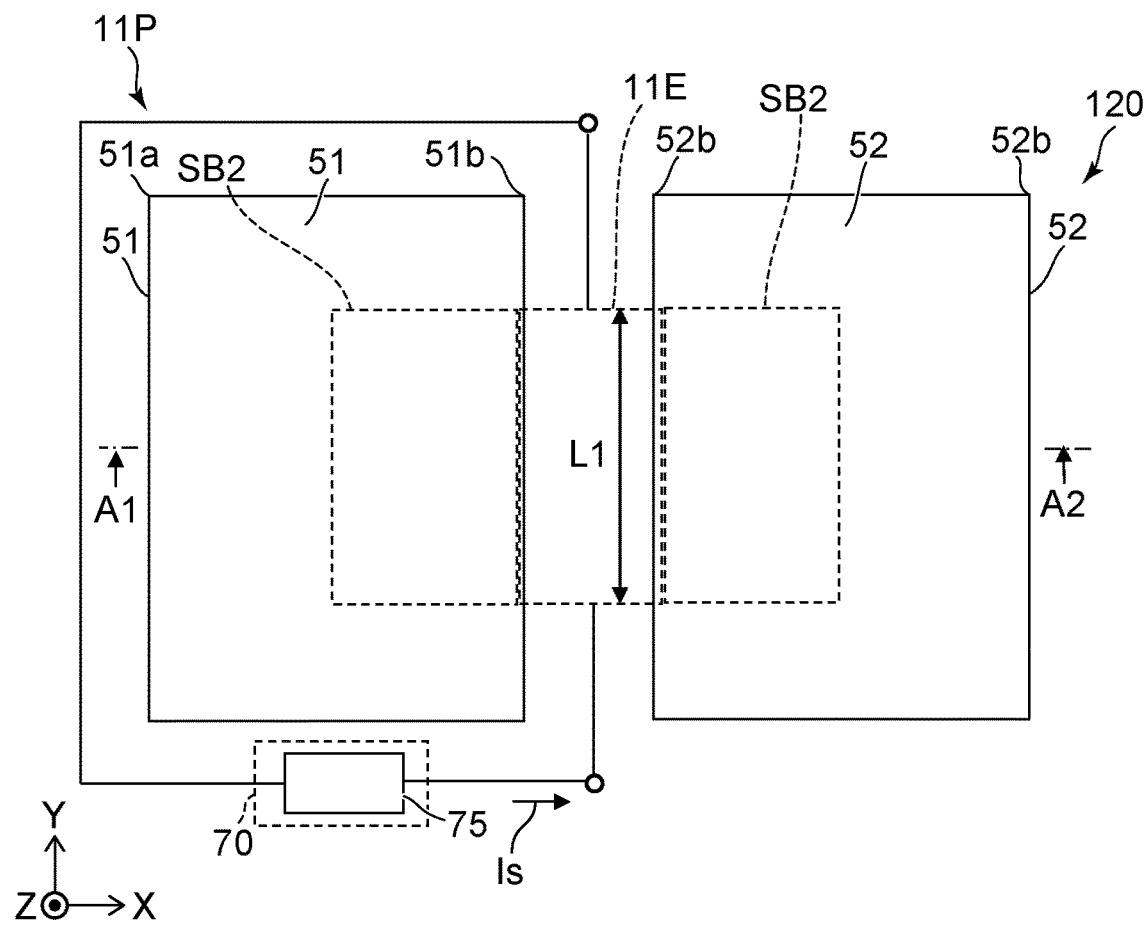

FIGS. 10A and 10B are schematic views illustrating the magnetic sensor according to the second embodiment.

FIG. 10A is a cross-sectional view taken along line A1-A2 of FIG. 10B. FIG. 10B is a plan view. In these figures, some elements have been omitted to make the figures easier to read.

As shown in FIGS. 10A and 10B, the magnetic sensor 120 according to the embodiment includes the first element part 11P.

The first element part 11P includes a first magnetic element 11E, a first side magnetic layer 31, a second side magnetic layer 32, a first magnetic member 51, and a second magnetic member 52. The first magnetic element 11E includes a first magnetic layer 11, a first counter magnetic layer 11o, and a first non-magnetic layer 11n. The first non-magnetic layer 11n is provided between the first magnetic layer 11 and the first counter magnetic layer 11o. For example, the stacking order of the first magnetic layer 11 and the first counter magnetic layer 11o is arbitrary.

At least a part of the first magnetic element 11E is between the first side magnetic layer 31 and the second side magnetic layer 32 in the second direction crossing the first direction. The second direction is, for example, the X-axis direction.

The direction from the first side magnetic layer 31 to the first magnetic member 51 is along the first direction (Z-axis direction). The direction from the second side magnetic layer 32 to the second magnetic member 52 is along the first direction. The direction from the first magnetic element 11E to the region 66a between the first magnetic member 51 and the second magnetic member 52 is along the first direction.

The first magnetic layer 11 and the first counter magnetic layer 11o include a first material. The first material includes Fe and Co. The first magnetic layer 11 and the first counter magnetic layer 11o are, for example, ferromagnetic layers.

The materials of the first side magnetic layer 31 and the second side magnetic layer 32 are different from the materials of the first magnetic layer 11 and the first counter magnetic layer 11o. The first side magnetic layer 31 and the second side magnetic layer 32 include a second material. The second material is different from the first material. For example, the second material includes at least one of a third material including Fe and Ni, and a fourth material. The fourth material is amorphous or has a crystallinity lower than that of the first material. For example, the size of the crystal grains in a material with low crystallinity is smaller than the size of the crystal grains in a material with high crystallinity. For example, the electric resistivity of the first side magnetic layer 31 and the second side magnetic layer 32 is higher than the electric resistivity of the first magnetic layer 11 and the first counter magnetic layer 11o.

For example, the current flowing through the first magnetic element 11E does not substantially flow through the first side magnetic layer 31. The current flowing through the first magnetic element 11E does not substantially flow through the second side magnetic layer 32. The first side magnetic layer 31 and the second side magnetic layer 32 do not affect the electric resistance of the first magnetic element 11E. The first side magnetic layer 31 and the second side magnetic layer 32 efficiently introduce the magnetic field collected by the first magnetic member 51 and the second magnetic member 52 into the first magnetic element 11E.

In the magnetic sensor 120, for example, the first side magnetic layer 31 is in contact with the first magnetic element 11E. For example, the second side magnetic layer 32 is in contact with the first magnetic element 11E. Since the electric resistance of the side magnetic layer is high, even when the side magnetic layer is the first magnetic element 11E, the influence on the change of the electric resistance Rx of the first magnetic element 11E can be suppressed.

For example, the distance between the first side magnetic layer 31 and the first magnetic element 11E may be 3 nm or less. The distance between the second side magnetic layer 32 and the first magnetic element 11E may be 3 nm or less. It is easy to obtain more stable electric separation.

In the embodiment, the first side magnetic layer 31 may be in contact with the first magnetic layer 11 and the first non-magnetic layer 11n. The second side magnetic layer 32 may be in contact with the first magnetic layer 11 and the first non-magnetic layer 11n. For example, it is easy to manufacture.

In the embodiment, the first side magnetic layer 31 may be in contact with the first counter magnetic layer 11o. The second side magnetic layer 32 may be in contact with the first counter magnetic layer 11o. For example, it is easy to manufacture.

As shown in FIG. 10A, the surface of the first magnetic element 11E facing the first side magnetic layer 31 may be inclined with respect to the Z-axis direction. The surface of the first magnetic element 11E facing the second side magnetic layer 32 may be inclined with respect to the Z-axis direction. For example, it is easy to manufacture.

Figure 11A:
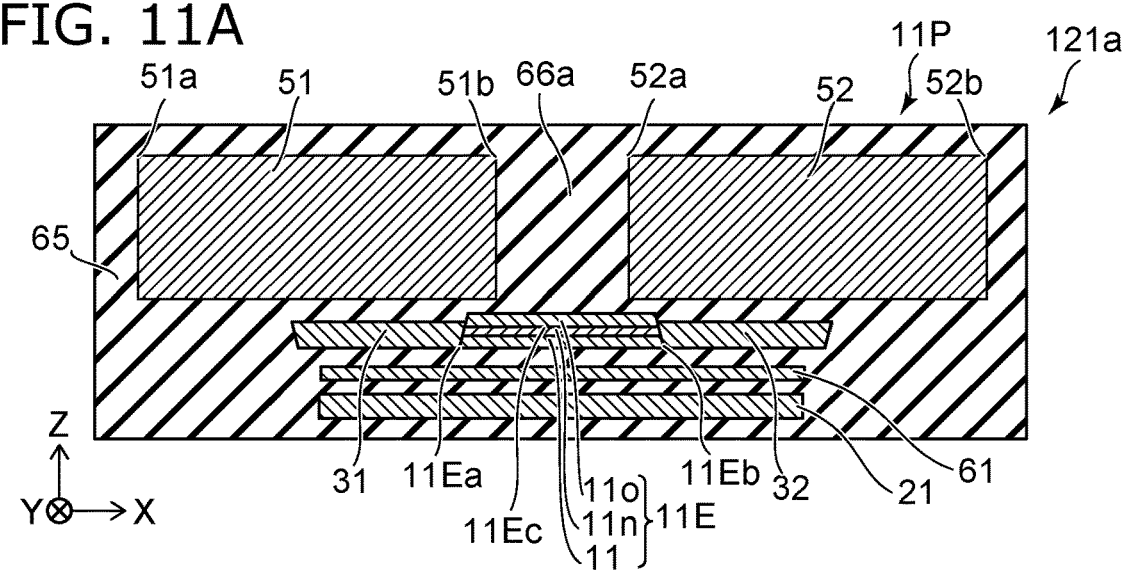
FIGS. 11A to 11C are schematic cross-sectional views illustrating the magnetic sensor according to the second embodiment.
Figure 11B:
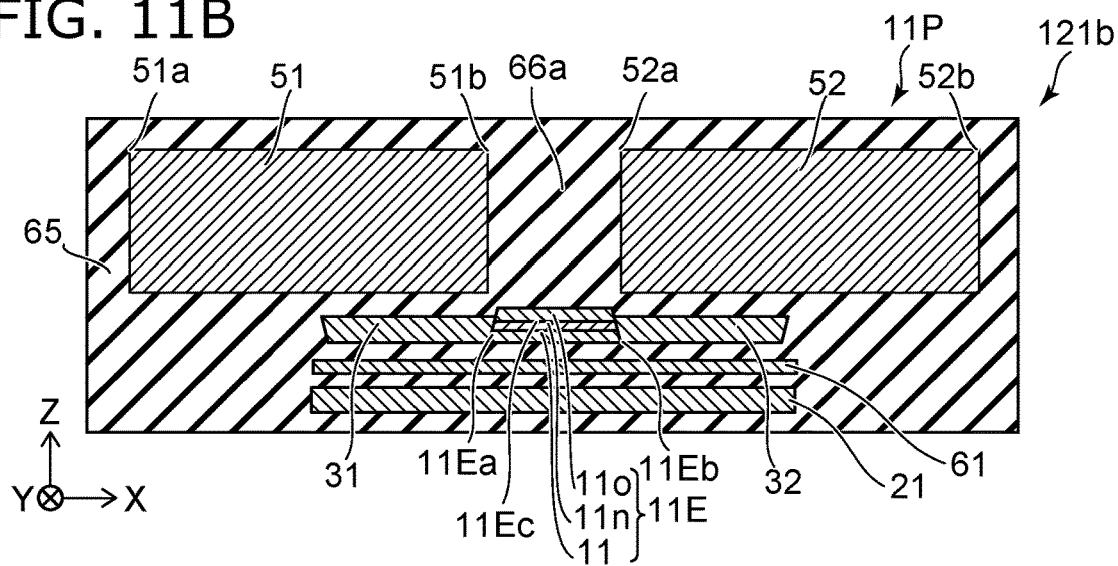
Figure 11C:
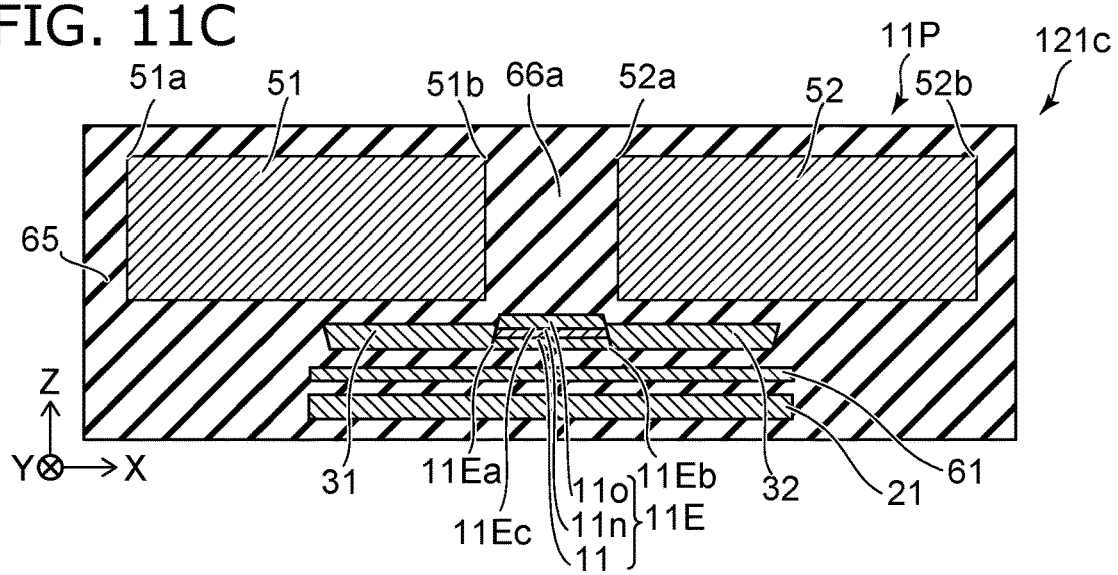

FIGS. 11A to 11C are schematic cross-sectional views illustrating the magnetic sensor according to the second embodiment.

As shown in FIGS. 11A to 11C, at least one of the first conductive member 21 and the first conductive portion 61 may be provided in the magnetic sensors 121a to 121c. For example, high-sensitivity detection using even functions is possible. For example, the influence of noise (for example, geomagnetism) can be suppressed.

As shown in FIG. 11A, in the magnetic sensor 121a, for example, the first magnetic element 11E includes a first superimposition region 11sa and a second superimposition region 11sb. The first superimposition region 11sa overlaps the first magnetic member 51 in the first direction (Z-axis direction). The second superimposition region 11sb overlaps the second magnetic member 52 in the first direction. For example, the length ws1 along the second direction (for example, the X-axis direction) of the first superimposition region 11sa is shorter than the length wSB1 along the second direction of the first structure SB1. The length ws2 of the second superimposition region 11sb along the second direction is shorter than the length wSB2 of the second structure SB2 along the second direction. For example, the length ws1 is not less than 0.01 times and not more than 0.9 times the length wSB1. For example, the length ws2 is not less than 0.01 times and not more than 0.9 times the length wSB2.

As shown in FIG. 11B, in the magnetic sensor 121b, for example, the first magnetic element end portion 11Ea overlaps the first magnetic member other end portion 51b in the first direction (Z-axis direction). The first magnetic element other end portion 11Eb overlaps the second magnetic member end portion 52a in the first direction. High sensitivity is obtained.

As shown in FIG. 11C, in the magnetic sensor 121c, for example, the position of the first magnetic element end portion 11Ea in the second direction (for example, the X-axis direction) is between the position of the first magnetic member other end portion 51b in the second direction and the position of the second magnetic member end portion 51a in the second direction. The position of the first magnetic element other end portion 11Eb in the second direction is between the position of the first magnetic member other end portion 51b in the second direction and the position of the second magnetic member end portion 52a in the second direction. High sensitivity is obtained.

Figure 12:
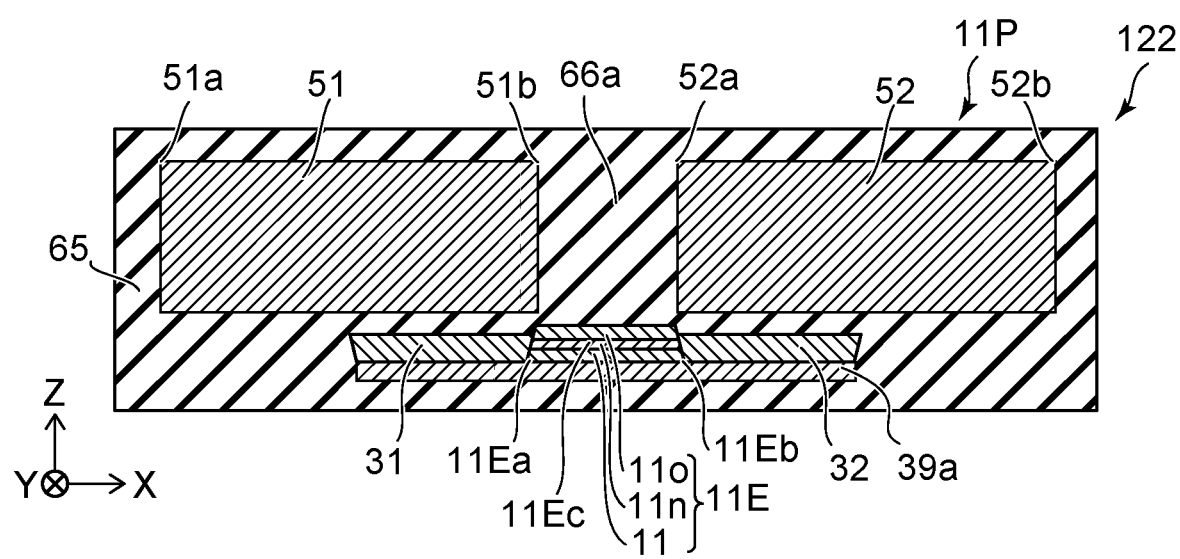
FIG. 12 is a schematic cross-sectional view illustrating the magnetic sensor according to the second embodiment.

FIG. 12 is a schematic cross-sectional view illustrating the magnetic sensor according to the second embodiment.

As shown in FIG. 12, in the magnetic sensor 122, the first element part 11P includes the first stacked magnetic layer 39a. Other configurations of the magnetic sensor 122 may be the same as those of the magnetic sensor 120.

In the magnetic sensor 122, the first side magnetic layer 31 is between a part of the first stacked magnetic layer 39a and the first magnetic member 51. The second side magnetic layer 32 is between another part of the first stacked magnetic layer 39a and the second magnetic member 52. The first magnetic element 11E is between the first stacked magnetic layer 39a and the region 66a between the first magnetic member 51 and the second magnetic member 52.

In one example, the first stacked magnetic layer 39a is in contact with the first magnetic element 11E. The magnetic field is collected by the first stacked magnetic layer 39a. The collected magnetic field is applied to the first magnetic element 11E. Higher sensitivity detection is possible.

The material of the first stacked magnetic layer 39a is different from the material of the first magnetic layer 11 and the first counter magnetic layer 11o. The first stacked magnetic layer 39a includes, for example, a second material. For example, the second material includes at least one of a third material including Fe and Ni, and a fourth material. The fourth material is amorphous or has crystallinity lower than that of the first material. For example, the size of the crystal grains in a material with low crystallinity is smaller than the size of the crystal grains in a material with high crystallinity. For example, the electric resistivity of the first stacked magnetic layer 39a is higher than the electric resistivity of the first magnetic layer 11 and the first counter magnetic layer 11o. The magnetic field can be efficiently applied to the first magnetic element 11E by the first stacked magnetic layer 39a while suppressing the influence on the current flowing through the first magnetic element 11E.

Figure 13A:
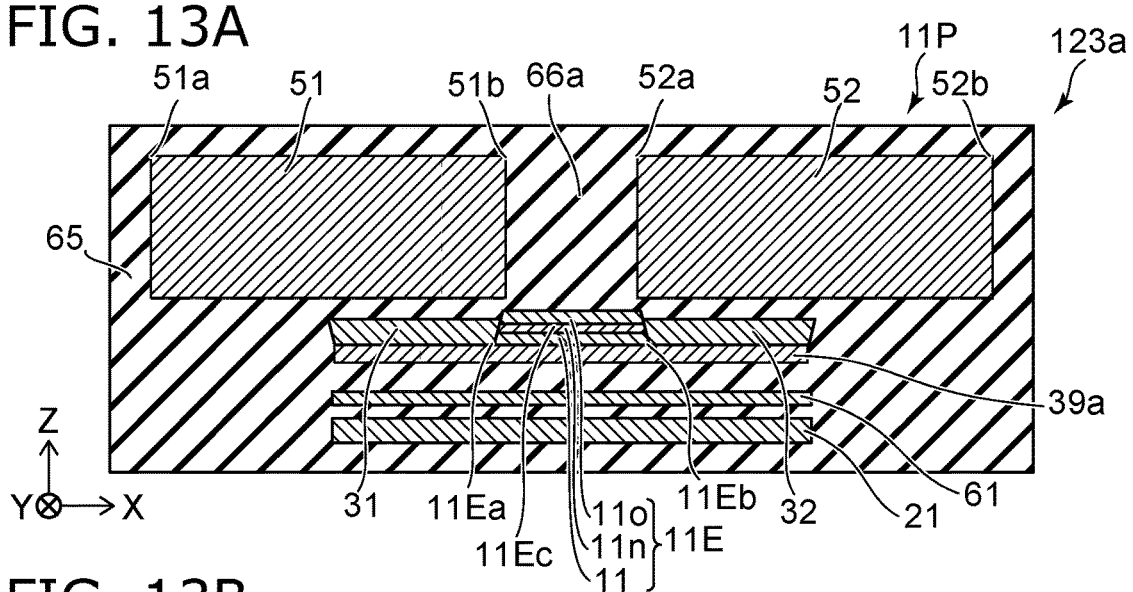
FIGS. 13A to 13C are schematic cross-sectional views illustrating the magnetic sensor according to the second embodiment.
Figure 13B:
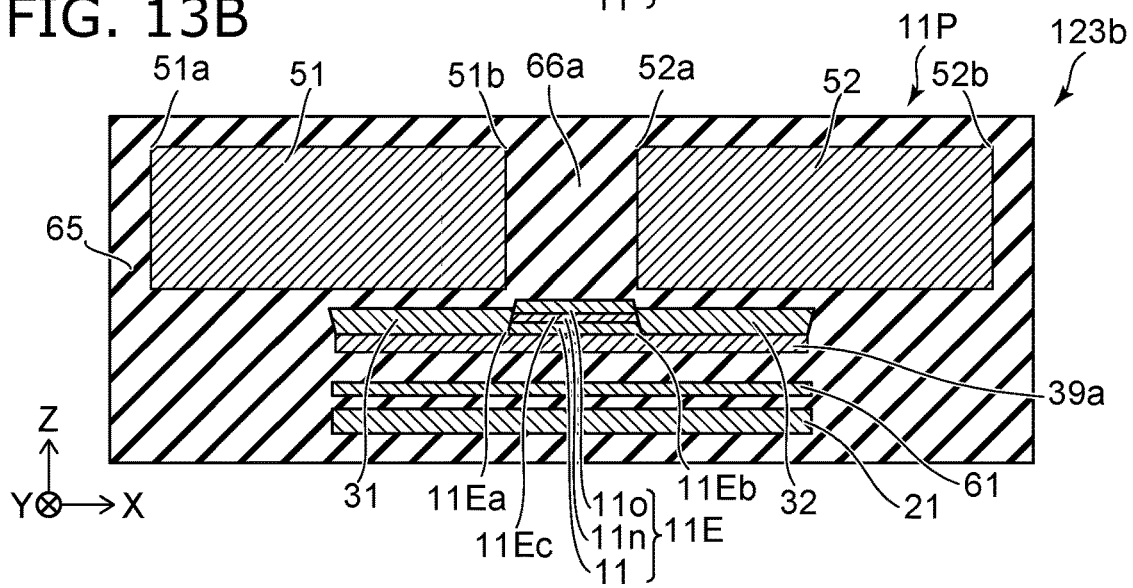
Figure 13C:
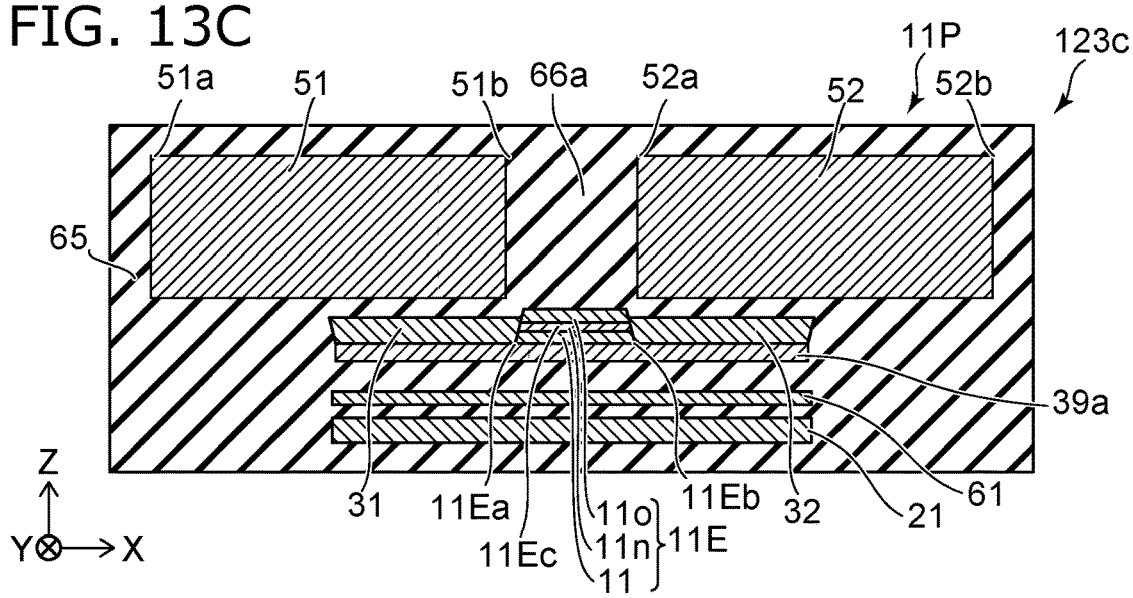

FIGS. 13A to 13C are schematic cross-sectional views illustrating the magnetic sensor according to the second embodiment.

As shown in FIGS. 13A to 13C, at least one of the first conductive member 21 and the first conductive portion 61 may be provided in the magnetic sensors 123a to 123c. For example, high-sensitivity detection using even functions is possible. For example, the influence of noise (for example, geomagnetism) can be suppressed.

As shown in FIG. 13A, in the magnetic sensor 123a, for example, the first superimposition region 11sa overlaps the first magnetic member 51 in the first direction (Z-axis direction). The second superimposition region 11sb overlaps the second magnetic member 52 in the first direction. For example, the length ws1 along the second direction (for example, the X-axis direction) of the first superimposition region 11sa is shorter than the length wSB1 along the second direction of the first structure SB1. The length ws2 of the second superimposition region 11sb along the second direction is shorter than the length wSB2 of the second structure SB2 along the second direction. For example, the length ws1 is not less than 0.01 times and not more than 0.9 times the length wSB1. For example, the length ws2 is not less than 0.01 times and not more than 0.9 times the length wSB2.

As shown in FIG. 13B, in the magnetic sensor 123b, for example, the first magnetic element end portion 11Ea overlaps the first magnetic member other end portion 51b in the first direction (Z-axis direction). The first magnetic element other end portion 11Eb overlaps the second magnetic member end portion 52a in the first direction. High sensitivity is obtained.

As shown in FIG. 13C, in the magnetic sensor 123c, for example, the position of the first magnetic element end portion 11Ea in the second direction (for example, the X-axis direction) is between the position of the first magnetic member other end portion 51b in the second direction and the position of the second magnetic member end portion 51a in the second direction. The position of the first magnetic element other end portion 11Eb in the second direction is between the position of the first magnetic member other end portion 51b in the second direction and the position of the second magnetic member end portion 52a in the second direction. High sensitivity is obtained.

Third Embodiment

Figure 14:
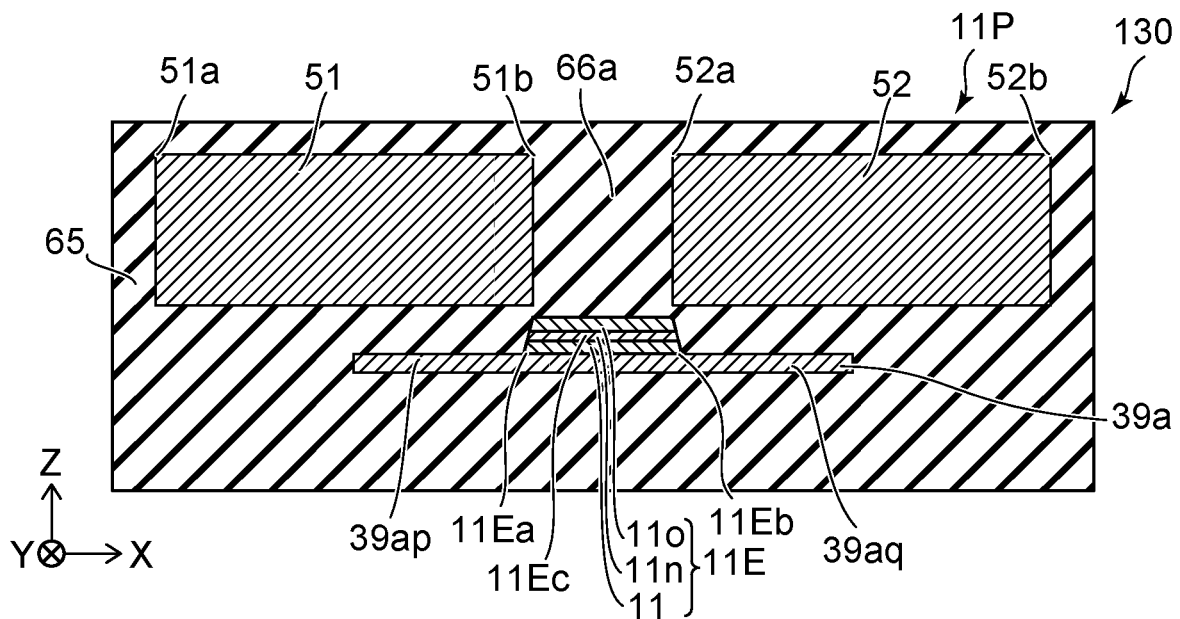
FIG. 14 is a schematic cross-sectional view illustrating a magnetic sensor according to a third embodiment.

FIG. 14 is a schematic cross-sectional view illustrating the magnetic sensor according to the third embodiment.

As shown in FIG. 14, the magnetic sensor 130 according to the embodiment includes the first element part 11P. The first element part 11P includes a first magnetic element 11E, a first stacked magnetic layer 39a, a first magnetic member 51, and a second magnetic member 52. The first magnetic element 11E includes a first magnetic layer 11, a first counter magnetic layer 11o, and a first non-magnetic layer 11n provided between the first magnetic layer 11 and the first counter magnetic layer 11o. The direction from the first magnetic layer 11 to the first counter magnetic layer 11o is along the first direction (Z-axis direction). The direction from a part 39ap of the first stacked magnetic layer 39a to the first magnetic member 51 is along the first direction (Z-axis direction). The direction from another part 39aq of the first stacked magnetic layer 39a to the second magnetic member 52 is along the first direction.

The direction from the first magnetic element 11E to the region 66a between the first magnetic member 51 and the second magnetic member 52 is along the first direction (Z-axis direction). The first magnetic element 11E is between the first stacked magnetic layer 39a and the above-mentioned region 66a. For example, the position of the first magnetic element 11E in the first direction (Z-axis direction) is between the position of the first stacked magnetic layer 39a in the first direction and the position of the first magnetic member 51 in the first direction.

The first magnetic layer 11 and the first counter magnetic layer 11o include a first material including Fe and Co. The first magnetic layer 11 and the first counter magnetic layer 11o are, for example, ferromagnetic layers. The material of the first stacked magnetic layer 39a is different from the material of the first magnetic layer 11 and the first counter magnetic layer 11o. The first stacked magnetic layer 39a includes a second material. The second material is different from the first material. The second material includes at least one of a third material including Fe and Ni and a fourth material. The fourth material is amorphous or has crystallinity lower than that of the first material. For example, the electric resistance of the first stacked magnetic layer 39a is higher than the electric resistance of the first magnetic layer 11 and higher than the electric resistance of the first counter magnetic layer 11o.

For example, the magnetic field can be efficiently applied to the first magnetic element 11E by the first stacked magnetic layer 39a while suppressing the influence on the current flowing through the first magnetic element 11E. High sensitivity is obtained.

Figure 15:
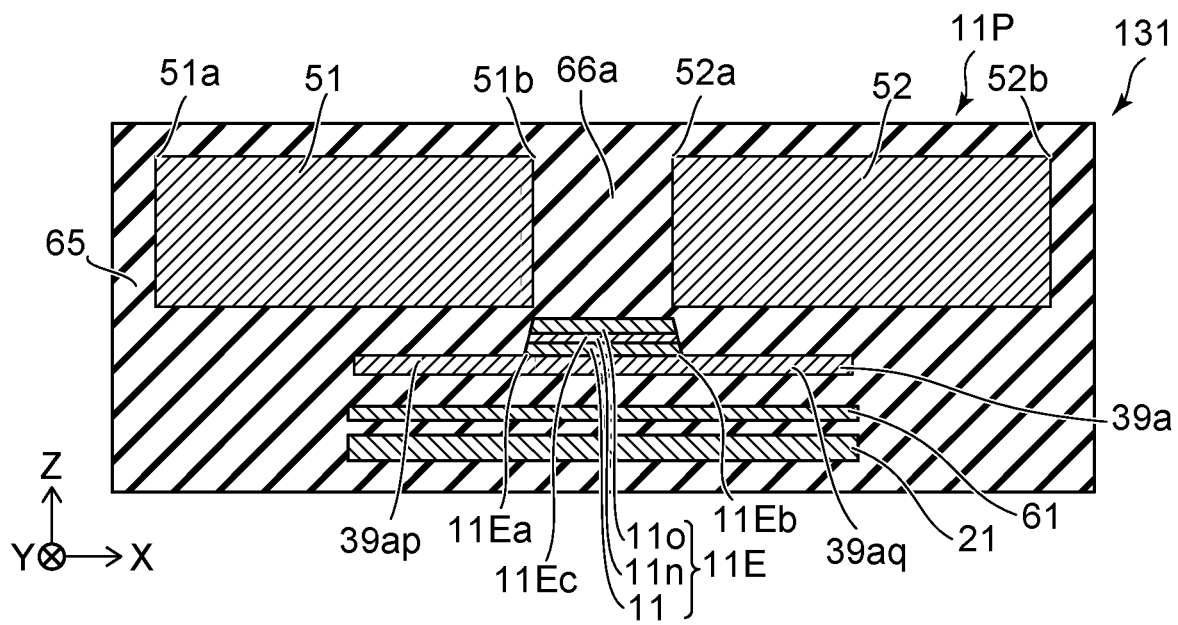
FIG. 15 is a schematic cross-sectional view illustrating the magnetic sensor according to the third embodiment.

FIG. 15 is a schematic cross-sectional view illustrating the magnetic sensor according to the third embodiment.

As shown in FIG. 15, at least one of the first conductive member 21 and the first conductive portion 61 may be provided in the magnetic sensor 131. For example, high-sensitivity detection using even functions is possible. For example, the influence of noise (for example, geomagnetism) can be suppressed.

In the magnetic sensor 130 or the magnetic sensor 131, the position of the end portion of the first magnetic element 11E may be the same as that of the magnetic sensors 123a to 123c.

In the second embodiment and the third embodiment, similarly to the first embodiment, the first magnetic element 11E has the characteristics of even functions (See FIGS. 6A, 6B, and FIG. 7B).

Fourth Embodiment

Figure 16A:
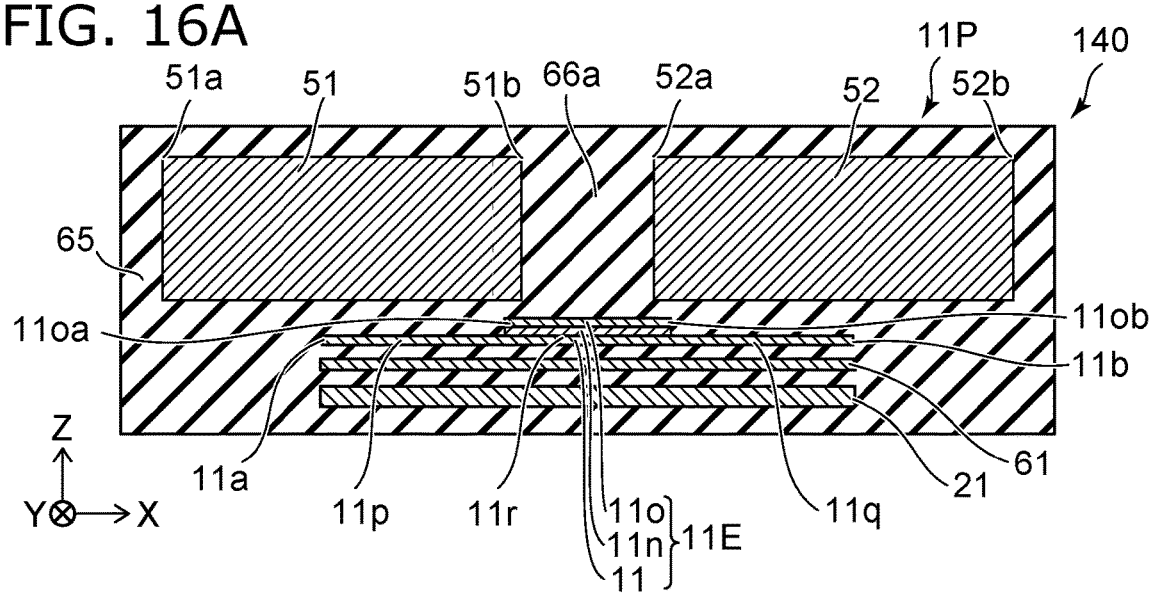
FIGS. 16A and 16B are schematic views illustrating a magnetic sensor according to a fourth embodiment.
Figure 16B:
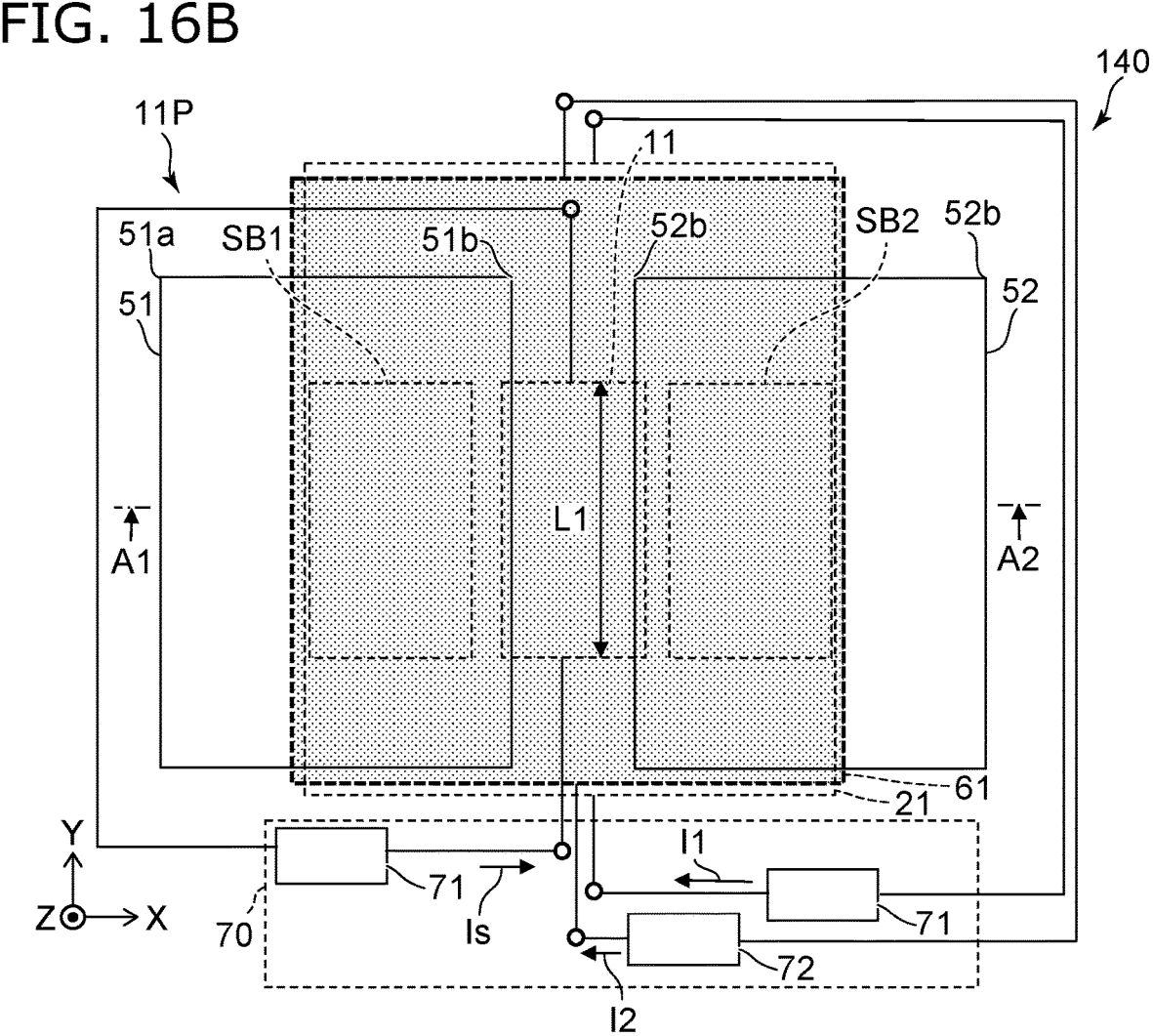

FIGS. 16A and 16B are schematic views illustrating the magnetic sensor according to the fourth embodiment.

FIG. 16A is a cross-sectional view taken along line A1-A2 of FIG. 16B. FIG. 16B is a plan view. In these figures, some elements have been omitted to make the figures easier to read.

As shown in FIGS. 16A and 16B, a magnetic sensor 140 according to the embodiment includes the first element part 11P. The first element part 11P includes the first magnetic element 11E, the first magnetic member 51, and the second magnetic member 52. The first magnetic element 11E includes the first magnetic layer 11, the first counter magnetic layer 11o, and the first non-magnetic layer 11n. The first non-magnetic layer 11n is provided between the first magnetic layer 11 and the first counter magnetic layer 11o. For example, the stacking order of the first magnetic layer 11 and the first counter magnetic layer 11o is arbitrary. The direction from the first magnetic layer 11 to the first counter magnetic layer 11o is along the first direction (Z-axis direction). The direction from a part 11p of the first magnetic layer 11 to the first magnetic member 51 is along the first direction (Z-axis direction). The direction from another part 11q of the first magnetic layer 11 to the second magnetic member 52 is along the first direction. The direction from the first counter magnetic layer 11o to the region 66a between the first magnetic member 51 and the second magnetic member 52 is along the first direction (Z-axis direction). The first magnetic layer 11 includes a portion (part 11r) between the above-mentioned part 11p and the above-mentioned another part 11q. In this example, the first counter magnetic layer 11o is between the above-mentioned part 11r and the above-mentioned region 66a in the Z-axis direction.

For example, the first magnetic member 51 includes the first magnetic member end portion 51a and the first magnetic member other end portion 51b. The second magnetic member 52 includes the second magnetic member end portion 52a and the second magnetic member other end portion 52b. In the second direction, there is a first magnetic member other end portion 51b between the first magnetic member end portion 51a and the second magnetic member other end portion 52b. The second direction crosses the first direction. The second direction is, for example, the X-axis direction. In the second direction (X-axis direction), there is the second magnetic member end portion 52a between the first magnetic member other end portion 51b and the second magnetic member other end portion 52b.

The first magnetic layer 11 includes a first magnetic layer end portion 11a and a first magnetic layer other end portion 11b. The position of the first magnetic layer end portion 11a in the second direction (for example, the X-axis direction) is between the position of the first magnetic member end portion 51a in the second direction and the position of the first magnetic member other end portion 51b in the second direction. The position of the first magnetic layer other end portion 11b in the second direction is between the position of the second magnetic member end portion 52a in the second direction and the position of the second magnetic member other end portion 52b in the second direction.

The first counter magnetic layer 11o includes a first counter magnetic layer end portion 11oa and a first counter magnetic layer other end portion 11ob. The position of the first counter magnetic layer end portion 11oa in the second direction (X-axis direction) is between the position of the first magnetic layer end portion 11a in the second direction and the position of the second magnetic member end portion 52a in the second direction. The position of the first counter magnetic layer other end portion 11ob in the second direction is between the position of the first magnetic member other end portion 51b in the second direction and the position of the first magnetic layer other end portion 11b in the second direction.

In the magnetic sensor 140, the electric resistance Rx of the first magnetic element 11E changes by an even function with respect to the magnetic field applied to the first magnetic element 11E. In the magnetic sensor 140, the first magnetic element 11E has the characteristics described with respect to, for example, FIGS. 6A, 6B and 7B.

In the magnetic sensor 140, the first conductive member 21 is provided. For example, high-sensitivity detection using even functions is possible. The first conductive portion 61 may be provided in the magnetic sensor 140. For example, the influence of noise (for example, geomagnetism) can be suppressed.

For example, the part 11p of the first magnetic layer 11 does not overlap the first counter magnetic layer 11o, but overlaps the first magnetic member 51. The another part 11q of the first magnetic layer 11 does not overlap the first counter magnetic layer 11o, but overlaps the second magnetic member 52. The magnetic fields collected by the first magnetic member 51 and the second magnetic member 52 are efficiently applied to the part 11p and the part 11q. The part 11p and the part 11q have a small effect on the electric resistance of the first magnetic element 11E. High sensitivity can be obtained in the magnetic sensor 140.

Figure 17A:
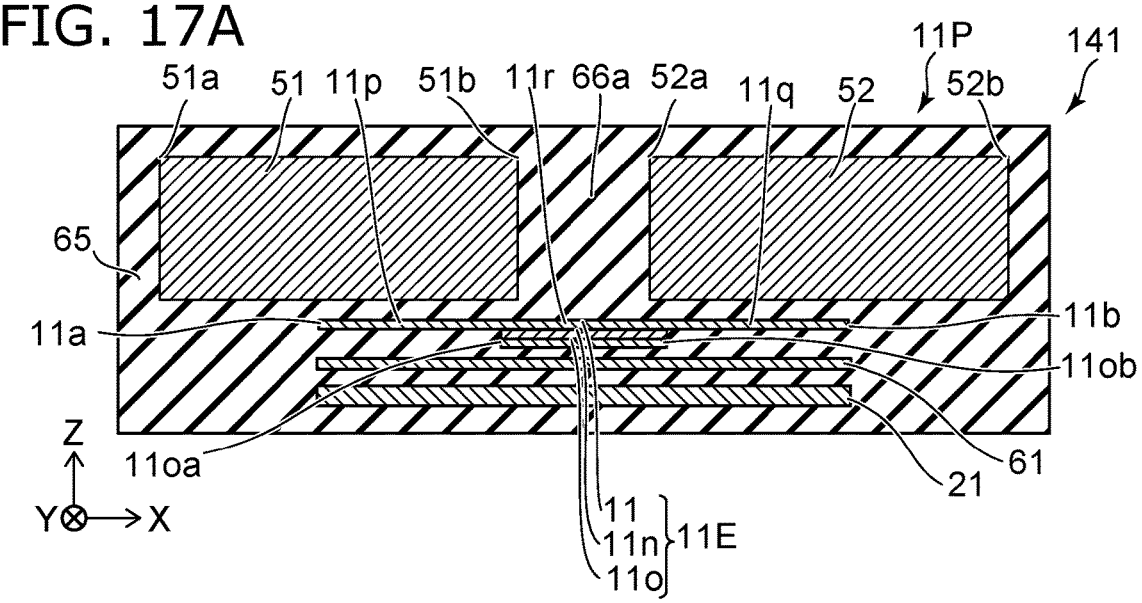
FIGS. 17A and 17B are schematic views illustrating the magnetic sensor according to the fourth embodiment.
Figure 17B:
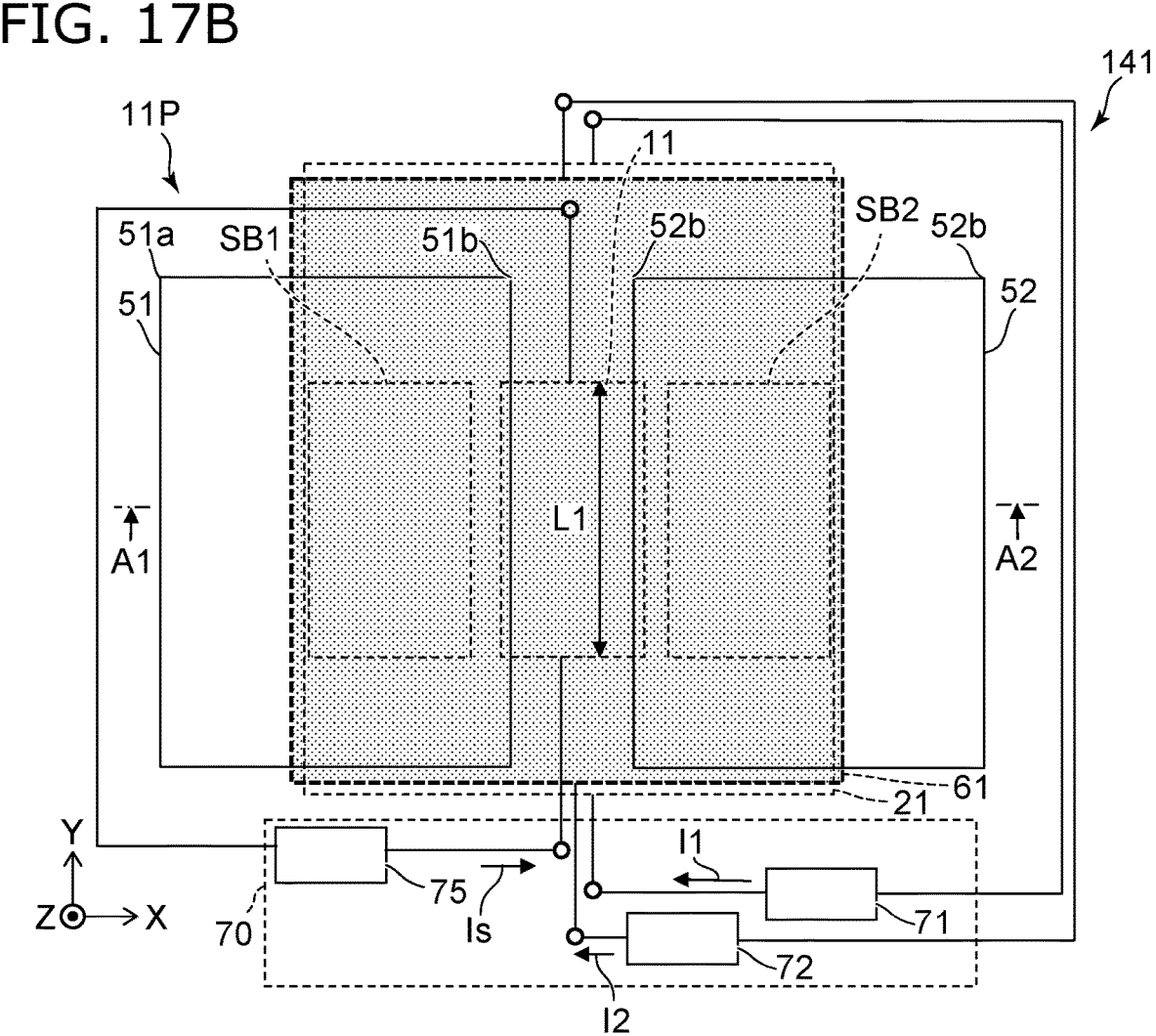

FIGS. 17A and 17B are schematic views illustrating the magnetic sensor according to the fourth embodiment.

FIG. 17A is a sectional view taken along line A1-A2 of FIG. 17B. FIG. 17B is a plan view. In these figures, some elements have been omitted to make the figures easier to read.

As shown in FIGS. 17A and 17B, a magnetic sensor 141 according to the embodiment includes the first element part 11P. The first element part 11P includes the first magnetic element 11E, the first magnetic member 51, and the second magnetic member 52. In the magnetic sensor 141, the portion (part 11r) between the part 11p of the first magnetic layer 11 and the another part 11q of the first magnetic layer 11 is between the first counter magnetic layer 11o and the region 66a between the first magnetic member 51 and the second magnetic member 52 in the Z-axis direction. Also in the magnetic sensor 141, the direction from the part 11p of the first magnetic layer 11 to the first magnetic member 51 is along the first direction (Z-axis direction). The direction from the another part 11q of the first magnetic layer 11 to the second magnetic member 52 is along the first direction.

Also in the magnetic sensor 141, the electric resistance Rx of the first magnetic element 11E changes by an even function with respect to the magnetic field applied to the first magnetic element 11E. For example, in the magnetic sensor 141, the first conductive member 21 is provided. For example, high-sensitivity detection using even functions is possible. The first conductive portion 61 may be provided in the magnetic sensor 141. For example, the influence of noise (for example, geomagnetism) can be suppressed. High sensitivity can also be obtained with the magnetic sensor 141.

Fifth Embodiment

FIGS. 18A, 18B, and 19A to 19C are schematic views illustrating a magnetic sensor according to a fifth embodiment.

Figure 18A:
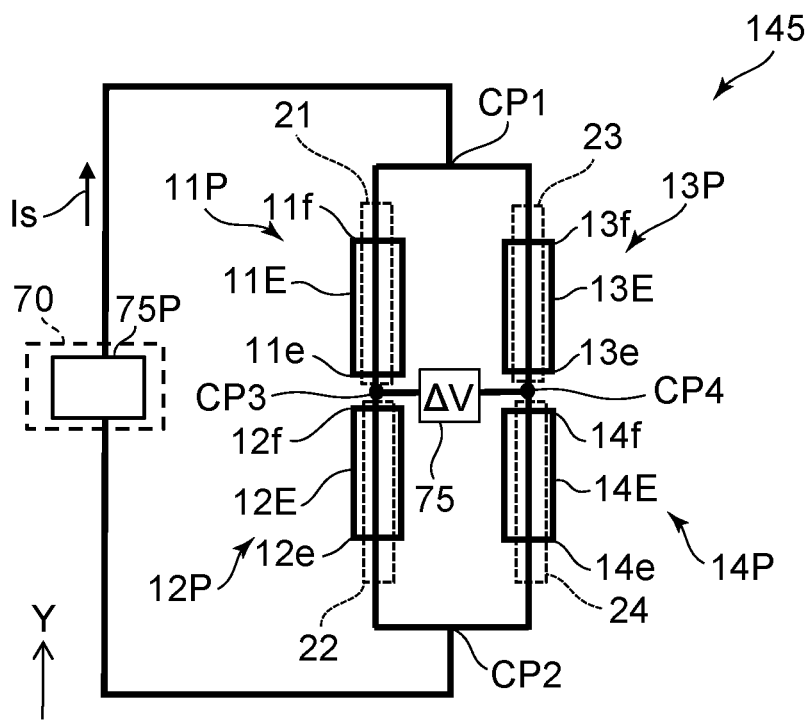
FIGS. 18A and 18B are schematic views illustrating a magnetic sensor according to a fifth embodiment.
Figure 18B:
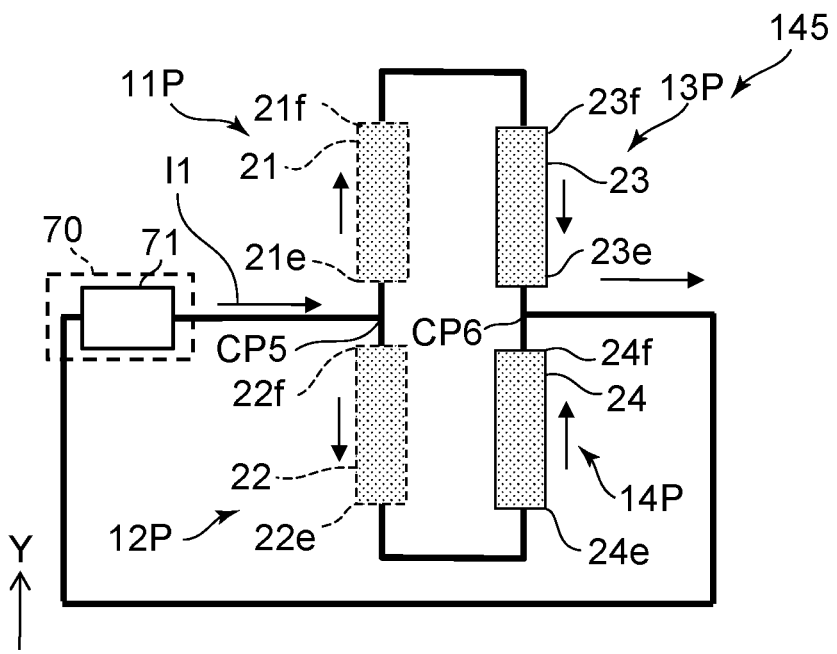
Figure 19A:
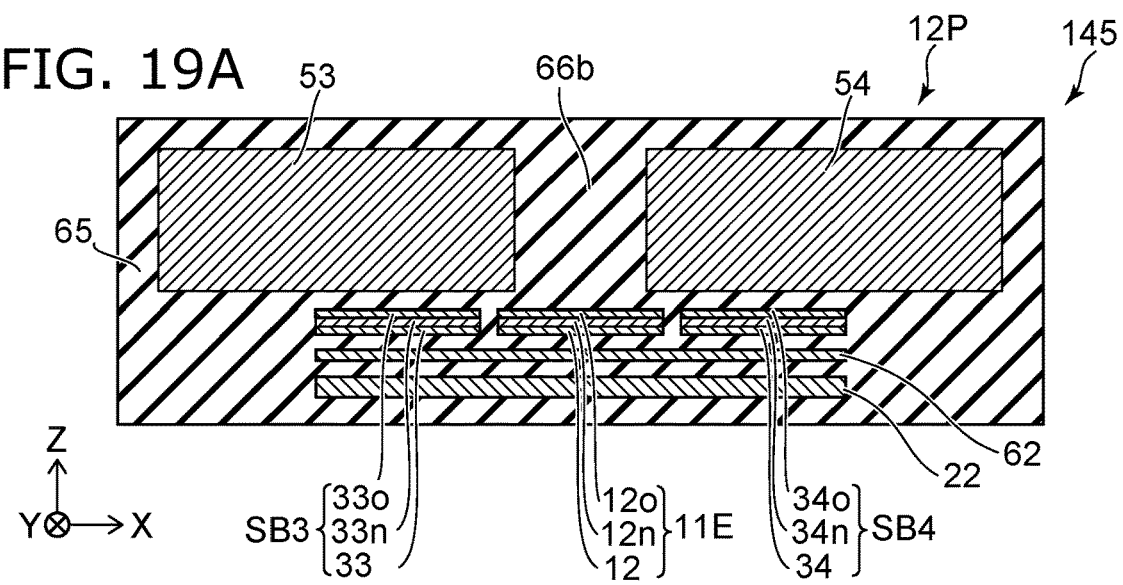
FIGS. 19A to 19C are schematic views illustrating the magnetic sensor according to the fifth embodiment.
Figure 19B:
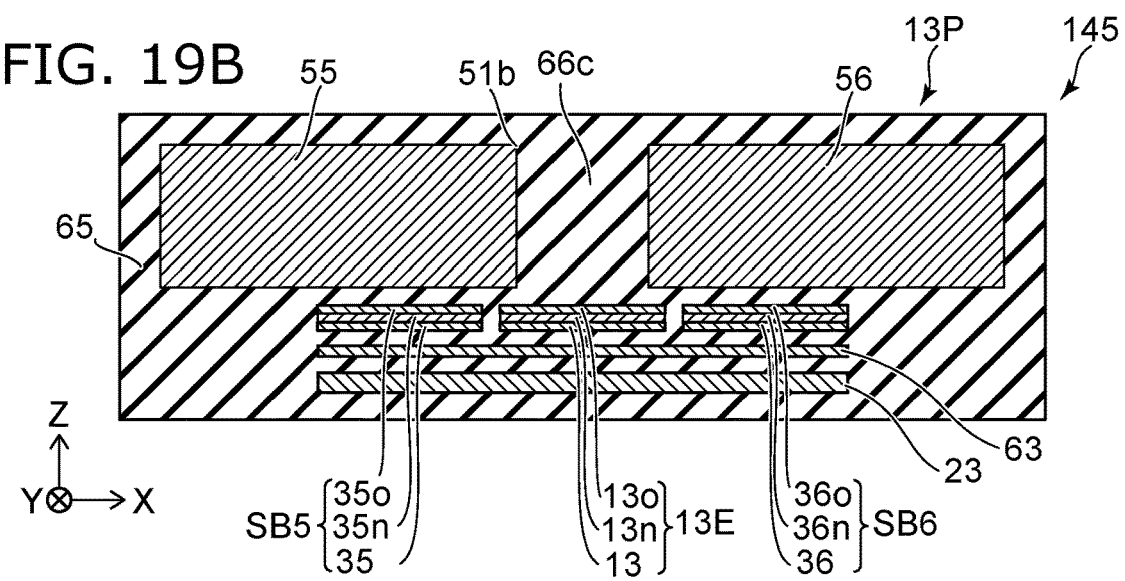
Figure 19C:
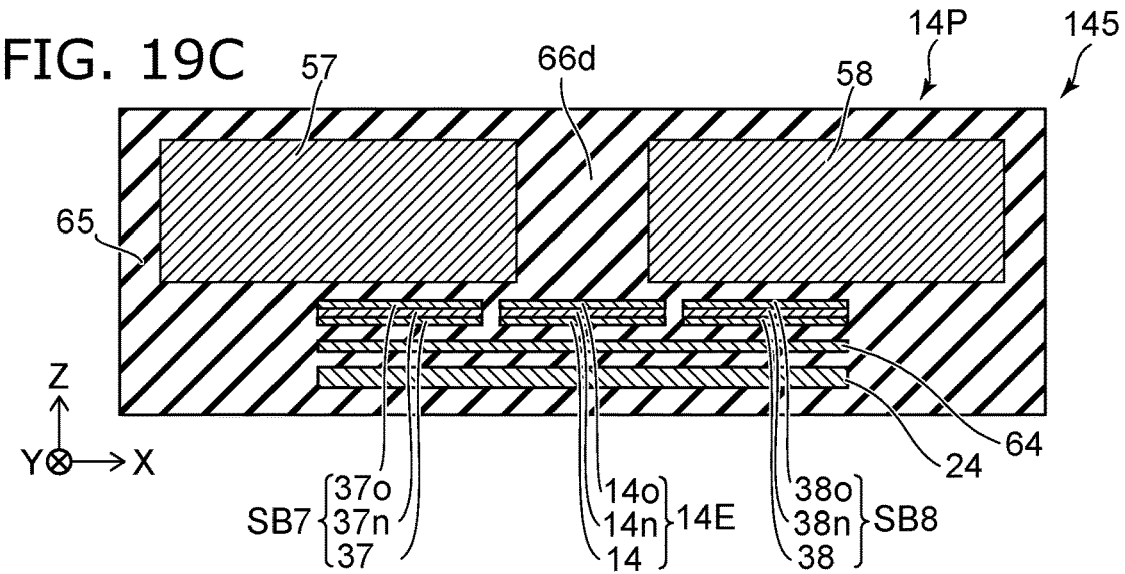

FIGS. 18A and 18B are schematic plan views. FIGS. 19A to 19C are schematic cross-sectional views.

As shown in FIG. 18A, a magnetic sensor 145 according to the embodiment includes first to fourth element parts 11P to 14P. The configuration of the second to fourth element parts 12P to 14P may be the same as the configuration of the first element part 11P described with respect to the first to fourth embodiments. Hereinafter, an example in which the first magnetic element 11E in the magnetic sensor 112 according to the first embodiment is used as the magnetic element will be described.

As shown in FIG. 18A, the first to fourth element parts 11P to 14P are bridge-connected. As a result, noise is further suppressed and higher sensitivity can be detected.

As shown in FIG. 19A, the second element part 12P includes a second magnetic element 12E, a third magnetic member 53, and a fourth magnetic member 54. The second magnetic element 12E includes a second magnetic layer 12, a second counter magnetic layer 12o, and a second nonmagnetic layer 12n provided between the second magnetic layer 12 and the second counter magnetic layer 12o. The direction from the second magnetic element 12E to the region 66b between the third magnetic member 53 and the fourth magnetic member 54 is along the first direction (Z-axis direction). In this example, the second element part 12P includes a third structure SB3 and a fourth structure SB4. The third structure SB3 includes a third side magnetic layer 33, a third side counter magnetic layer 33o, and a third side nonmagnetic layer 33n provided between the third side magnetic layer 33 and the third side counter magnetic layer 33o. The fourth structure SB4 includes a fourth side magnetic layer 34, a fourth side counter magnetic layer 34o, and a fourth side nonmagnetic layer 34n provided between the fourth side magnetic layer 34 and the fourth side counter magnetic layer 34o. In this example, the second element part 12P includes a second conductive member 22 and a second conductive portion 62.

As shown in FIG. 19B, the third element part 13P includes a third magnetic element 13E, a fifth magnetic member 55, and a sixth magnetic member 56. The third magnetic element 13E includes a third magnetic layer 13, a third counter magnetic layer 13o, and a third non-magnetic layer 13n provided between the third magnetic layer 13 and the third counter magnetic layer 13o. The direction from the third magnetic element 13E to the region 66c between the fifth magnetic member 55 and the sixth magnetic member 56 is along the first direction (Z-axis direction). In this example, the third element part 13P includes a fifth structure SB5 and a sixth structure SB6. The fifth structure SB5 includes a fifth side magnetic layer 35, a fifth side counter magnetic layer 35o, and a fifth side non-magnetic layer 35 provided between the fifth side magnetic layer 35 and the fifth side counter magnetic layer 35o. The sixth structure SB6 includes a sixth side magnetic layer 36, a sixth side counter magnetic layer 36o, and a sixth side non-magnetic layer 36 provided between the sixth side magnetic layer 36 and the sixth side counter magnetic layer 36o. In this example, the third element part 13P includes a third conductive member 23 and a third conductive portion 63.

As shown in FIG. 19C, the fourth element part 14P includes a fourth magnetic element 14E, a seventh magnetic member 57, and an eighth magnetic member 58. The fourth magnetic element 14E includes a fourth magnetic layer 14, a fourth counter magnetic layer 14o, and a fourth nonmagnetic layer 14n provided between the fourth magnetic layer 14 and the fourth counter magnetic layer 14o. The direction from the fourth magnetic element 14E to the region 66d between a seventh magnetic member 57 and an eighth magnetic member is along the first direction (Z-axis direction). In this example, the fourth element part 14P includes a seventh structure SB7 and an eighth structure SB8. The seventh structure SB7 includes a seventh side magnetic layer 37, a seventh side counter magnetic layer 37o, and a seventh side non-magnetic layer 37n provided between the seventh side magnetic layer 37 and the seventh side counter magnetic layer 37o. The eighth structure SB8 includes an eighth side magnetic layer 38, an eighth side facing magnetic layer 38o, and an eighth side nonmagnetic layer 38n provided between the eighth side magnetic layer 38 and the eighth side counter magnetic layer 38o. In this example, the fourth element part 14P includes a fourth conductive member 24 and a fourth conductive portion 64.

As shown in FIG. 18A, one end 11e of the first magnetic element 11E is electrically connected to an other end 12f of the second magnetic element 12E. An other end 11f of the first magnetic element 11E is electrically connected to an other end 13f of the third magnetic element 13E. One end 12e of the second magnetic element 12E is electrically connected to one end 14e of the fourth magnetic element 14E. One end 13e of the third magnetic element 13E is electrically connected to an other end 14f of the fourth magnetic element 14E. The electrical connection point of the other end 11f of the first magnetic element 11E and the other end 13f of the third magnetic element 13E is defined as a first connection point CP1. The electrical connection point between the one end 12e of the second magnetic element 12E and the one end 14e of the fourth magnetic element 14E is defined as a second connection point CP2. A current circuit 76P is configured to supply the detected current Is between the first connection point CP1 and the second connection point CP2. The electrical connection point of the one end 11e of the first magnetic element 11E and the other end 12f of the second magnetic element 12E is defined as a third connection point CP3. The electrical connection point of the one end 13e of the third magnetic element 13E and the other end 14f of the fourth magnetic element 14E is defined as a fourth connection point CP4. A third circuit 73 is configured to detect the difference ΔV between the potential of the third connection point CP3 and the potential of the fourth connection point CP4.

As shown in FIG. 18B, one end 21e of the first conductive member 21 is electrically connected to an other end 22f of the second conductive member 22. An other end 21f of the first conductive member 21 is electrically connected to an other end 23f of the third conductive member 23. One end 22e of the second conductive member 22 is electrically connected to one end 24e of the fourth conductive member 24. One end 23e of the third conductive member 23 is electrically connected to an other end 24f of the fourth conductive member 24. The electrical connection point of the one end 21e of the first conductive member 21 and the other end 22f of the second conductive member 22 is defined as a fifth connection point CP5. The electrical connection point of the one end 23e of the third conductive member 23 and the other end 23f of the fourth conductive member 24 is defined as a sixth connection point CP6. A first circuit 71 supplies a first current I1 including an AC component between the fifth connection point CP5 and the sixth connection point CP6.

For example, the phase of the magnetic field applied to the first magnetic element 11E by the first current I1 supplied to the first conductive member 21 is the opposite of the phase of the applied magnetic field supplied to the third magnetic element 13E by the first current I1 supplied to the third conductive member 23. For example, the phase of the magnetic field applied to the second magnetic element 12E by the first current I1 supplied to the second conductive member 22 is opposite of the phase of the magnetic field applied to the fourth magnetic element 14E by the first current I1 supplied to the fourth conductive member 24. For example, the phase of the magnetic field applied to the first magnetic element 11E by the first current I1 supplied to the first conductive member 21 is opposite of the phase of the magnetic field supplied to the second magnetic element 12E by the first current I1 supplied to the second conductive member 22. With such a bridge circuit, the noise component is suppressed and higher sensitivity is obtained.

Sixth Embodiment

The sixth embodiment relates to an inspection device. As described later, the inspection device may include a diagnostic device.

Figure 20:
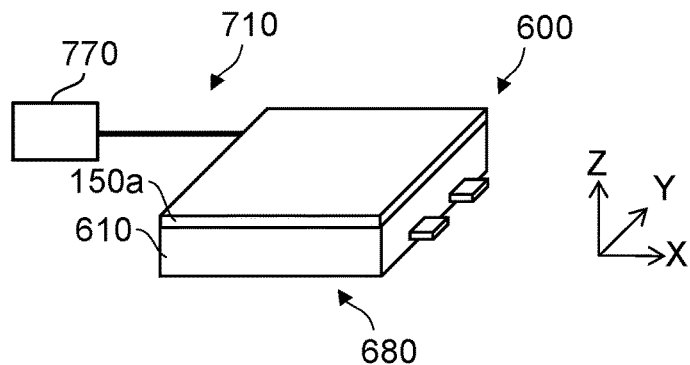
FIG. 20 is a schematic perspective view showing an inspection device according to a sixth embodiment.

FIG. 20 is a schematic perspective view showing the inspection device according to the sixth embodiment.

As shown in FIG. 20, the inspection device 710 according to the embodiment includes a magnetic sensor 150a and a processor 770. The magnetic sensor 150a may be the magnetic sensor according to any one of the first to fifth embodiments and a modification thereof. The processor 770 processes the output signal obtained from the magnetic sensor 150a. The processor 770 may compare the signal obtained from the magnetic sensor 150a with the reference value. The processor 770 can output the inspection result based on the processing result.

For example, the inspection device 710 inspects an inspection target 680. The inspection target 680 is, for example, an electronic device (including a semiconductor circuit or the like). The inspection target 680 may be, for example, a battery 610 or the like.

For example, the magnetic sensor 150a according to the embodiment may be used together with the battery 610. For example, a battery system 600 includes the battery 610 and the magnetic sensor 150a. The magnetic sensor 150a can detect the magnetic field generated by the current flowing through the battery 610.

Figure 21:
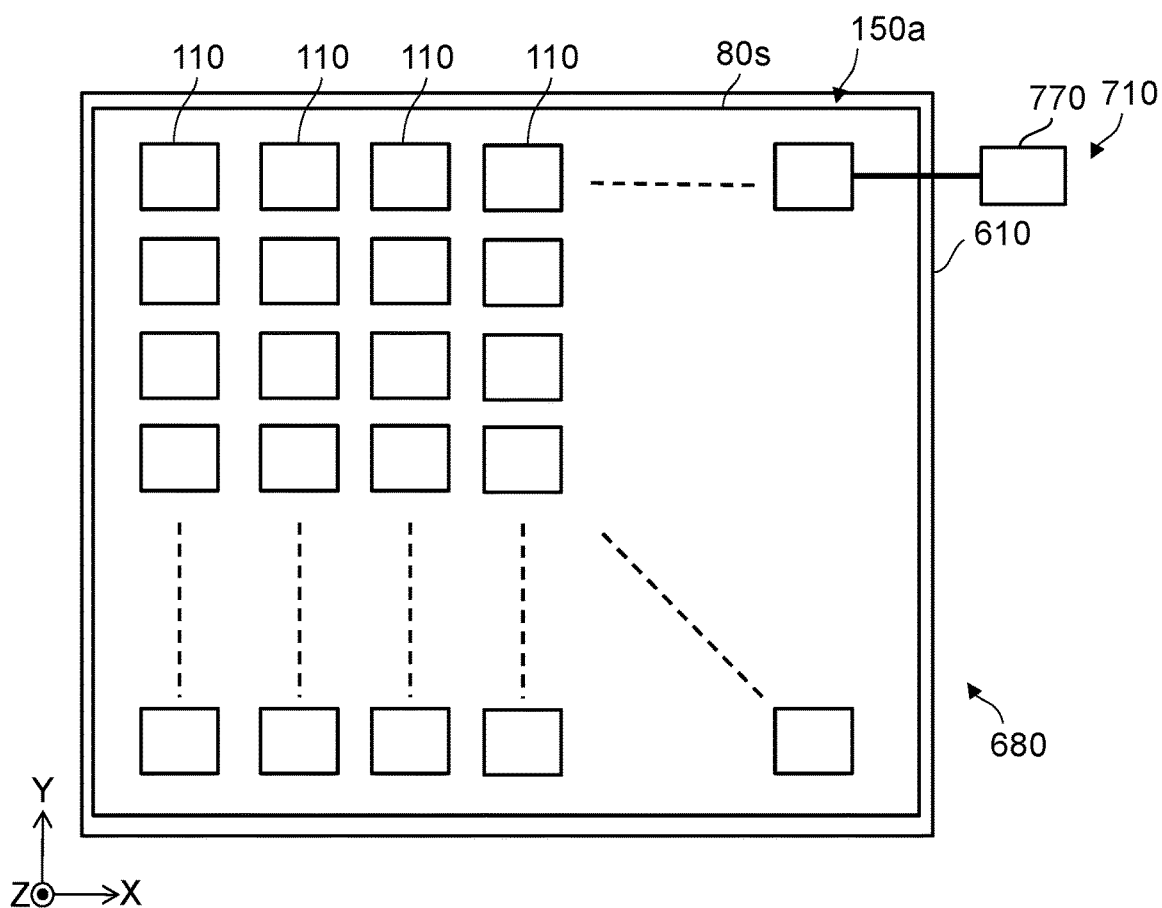
FIG. 21 is a schematic plan view showing the inspection device according to the sixth embodiment.

FIG. 21 is a schematic plan view showing the inspection device according to the sixth embodiment.

As shown in FIG. 21, the magnetic sensor 150a includes, for example, a plurality of magnetic sensors according to the embodiment. In this example, the magnetic sensor 150a includes a plurality of magnetic sensors (e.g., magnetic sensor 110, etc.). The plurality of magnetic sensors are arranged along, for example, two directions (for example, the X-axis direction and the Y-axis direction). The plurality of magnetic sensors 110 are provided, for example, on a substrate.

The magnetic sensor 150a can detect a magnetic field generated by a current flowing through the inspection target 680 (for example, the battery 610). For example, when the battery 610 approaches an abnormal state, an abnormal current may flow through the battery 610. By detecting the abnormal current with the magnetic sensor 150a, it is possible to know the change in the state of the battery 610. For example, in a state where the magnetic sensor 150a is placed close to the battery 610, the entire battery 610 can be inspected in a short time by using the sensor group driving means in two directions. The magnetic sensor 150a may be used for inspection of the battery 610 in the manufacture of the battery 610.

Figure 22:
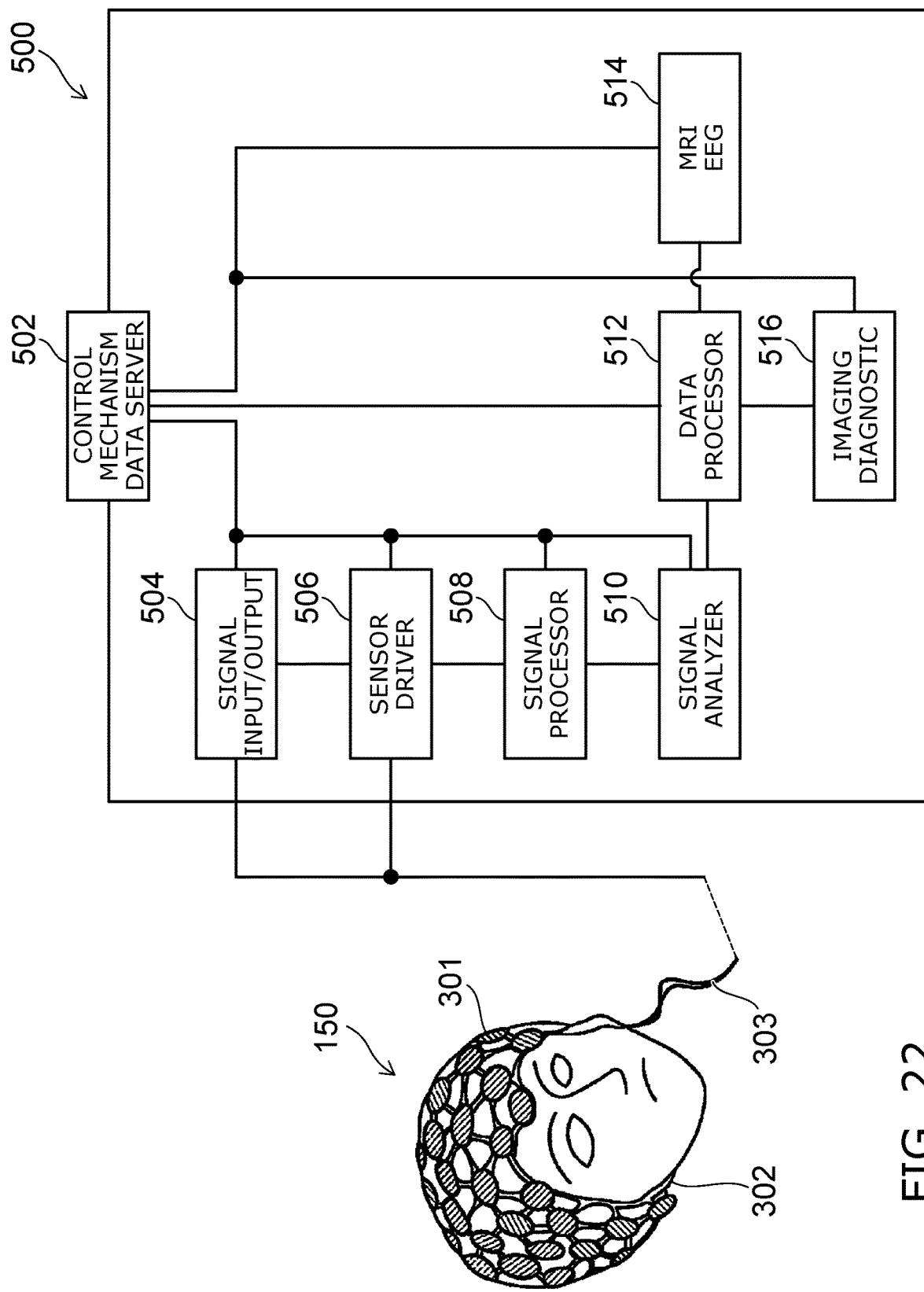
FIG. 22 is a schematic view showing a magnetic sensor and an inspection device according to a sixth embodiment.

The magnetic sensor according to the embodiment can be applied to, for example, the inspection device 710 such as a diagnostic device. FIG. 22 is a schematic view showing the magnetic sensor and the inspection device according to the sixth embodiment.

As shown in FIG. 22, a diagnostic device 500, which is an example of the inspection device 710, includes a magnetic sensor 150. The magnetic sensor 150 includes the magnetic sensors described with respect to the first to fifth embodiments, and modifications thereof.

In the diagnostic apparatus 500, the magnetic sensor 150 is, for example, a magnetoencephalograph. The magnetoencephalograph detects a magnetic field generated by cranial nerves. When the magnetic sensor 150 is used in a magnetoencephalograph, the size of the magnetic element included in the magnetic sensor 150 is, for example, not less than 1 mm and not more than 10 mm. This size is, for example, a length including the MFC.

As shown in FIG. 22, the magnetic sensor 150 (magnetoencephalogram) is attached to, for example, a head of a human body. The magnetic sensor 150 (magnetoencephalogram) includes a sensor part 301. The magnetic sensor 150 (magnetoencephalogram) may include a plurality of sensor parts 301. The number of the plurality of sensor parts 301 is, for example, about 100 (for example, not less than 50 and not more than 150). The plurality of sensor parts 301 are provided on a flexible base 302.

The magnetic sensor 150 may include, for example, a circuit such as differential detection. The magnetic sensor 150 may include a sensor other than the magnetic sensor (for example, a potential terminal or an acceleration sensor).

The size of the magnetic sensor 150 is smaller than the size of the conventional SQUID magnetic sensor. Therefore, it is easy to install the plurality of sensor parts 301. Installation of the plurality of sensor parts 301 and other circuits is easy. The coexistence of the plurality of sensor parts 301 and other sensors is easy.

The base 302 may include an elastic body such as a silicone resin. For example, a plurality of sensor parts 301 are connected to the base 302. The base 302 can be in close contact with the head, for example.

The input/output code 303 of the sensor part 301 is connected to a sensor drive part 506 and a signal input/output part 504 of the diagnostic device 500. The magnetic field measurement is performed in the sensor part 301 based on the electric power from the sensor drive part 506 and the control signal from the signal input/output part 504. The result is input to the signal input/output part 504. The signal obtained by the signal input/output part 504 is supplied to a signal processor 508. In the signal processor 508, for example, processing such as noise removal, filtering, amplification, and signal calculation is performed. The signal processed by the signal processor 508 is supplied to a signal analyzer 510. The signal analyzer 510 extracts, for example, a specific signal for magnetoencephalography measurement. In the signal analyzer 510, for example, signal analysis for matching the signal phases is performed.

The output of the signal analyzer 510 (data for which signal analysis has been completed) is supplied to the data processor 512. The data processor 512 performs data analysis. In this data analysis, for example, image data such as MRI (Magnetic Resonance Imaging) can be incorporated. In this data analysis, for example, scalp potential information such as EEG (Electroencephalogram) can be incorporated. By data analysis, for example, nerve ignition point analysis or inverse problem analysis is performed.

The result of the data analysis is supplied to, for example, an imaging diagnosis part 516. Imaging is performed in the imaging diagnosis part 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnostic device 500 according to the embodiment includes the magnetic sensor 150 and the processor that processes an output signal obtained from the magnetic sensor 150. This processor includes, for example, at least one of the signal processor 508 and the data processor 512. The processor includes, for example, a computer.

In the magnetic sensor 150 shown in FIG. 22, the sensor part 301 is installed on the head of the human body. The sensor part 301 may be installed on the chest of the human body. This enables magnetocardiographic measurement. For example, the sensor part 301 may be installed on the abdomen of a pregnant woman. This makes it possible to perform a fetal heartbeat test.

The magnetic sensor device including the subject is preferably installed in a shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with the shield mechanism. For example, effective shielding may be performed in signal analysis or data processing.

In embodiments, the base 302 may be flexible and may be substantially non-flexible. In the example shown in FIG. 22, the base 302 is a continuous film processed into a hat shape. The base 302 may have a net shape. Thereby, for example, good wearability can be obtained. For example, the adhesion of the base 302 to the human body is improved. The base 302 may be helmet-shaped and may be rigid.

Figure 23:
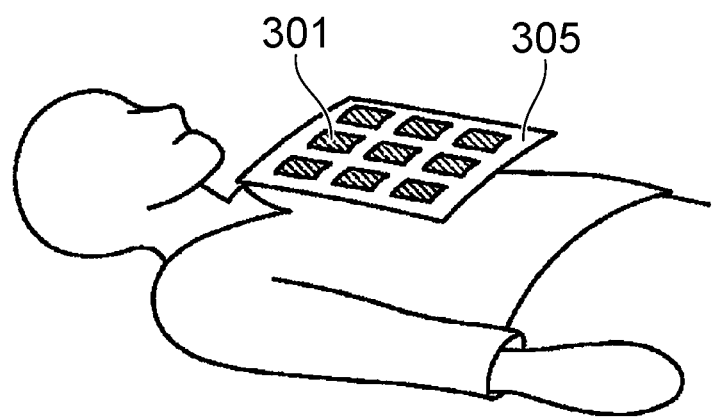
FIG. 23 is a schematic view showing the inspection device according to the sixth embodiment.

FIG. 23 is a schematic view showing the inspection device according to the sixth embodiment.

FIG. 23 is an example of a porcelain meter. In the example shown in FIG. 23, the sensor part 301 is provided on the flat plate-shaped hard base 305.

In the example shown in FIG. 23, the input/output of the signal obtained from the sensor part 301 is the same as the input/output described with respect to FIG. 23. In the example shown in FIG. 23, the processing of the signal obtained from the sensor part 301 is the same as the processing described with respect to FIG. 22.

There is a reference example of using a SQUID (Superconducting Quantum Interference Device) magnetic sensor as a device for measuring a weak magnetic field such as a magnetic field generated from a living body. In this reference example, since superconductivity is used, the device is large and the power consumption is large. The burden on the measurement target (patient) is heavy.

According to the embodiment, the device can be miniaturized. Power consumption can be suppressed. The burden on the measurement target (patient) can be reduced. According to the embodiment, the SN ratio of magnetic field detection can be improved. Sensitivity can be improved.

The embodiment may include the following configurations (for example, technical proposal).

(Configuration 1)

A magnetic sensor, comprising: a first element part, the first element part including
a first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction,
a first structure including a first side magnetic layer,
a second structure including a second side magnetic layer, the first magnetic element being between the first structure and the second structure in a second direction crossing the first direction, the first magnetic element being separated from the first side magnetic layer and the second side magnetic layer,
a first magnetic member, a direction from the first side magnetic layer toward the first magnetic member being along the first direction, and
a second magnetic member, a direction from the second side magnetic layer toward the second magnetic member being along the first direction,
a direction from the first magnetic element toward a region between the first magnetic member and the second magnetic member being along the first direction.

(Configuration 2)

The magnetic sensor according to Configuration 1, wherein
the first structure includes a first side counter magnetic layer and a firs side nonmagnetic layer,
a direction from the first side magnetic layer toward the first side counter magnetic layer is along the first direction,
the first side nonmagnetic layer is between the first side magnetic layer and the first side counter magnetic layer,
the second structure includes a second side counter magnetic layer and a second side nonmagnetic layer,
a direction from the second side magnetic layer toward the second side counter magnetic layer is along the first direction,
the second side nonmagnetic layer is between the second side magnetic layer and the second side counter magnetic layer, and
the first counter magnetic layer is between the first side counter magnetic layer and the second side counter magnetic layer.

(Configuration 3)

The magnetic sensor, according to Configuration 1 or 2, wherein
a distance along the second direction between the first magnetic layer and the first side magnetic layer is not less than 0.5 nm, and
a distance along the second direction between the first magnetic layer and the first side counter magnetic layer is not less than 0.5 nm.

(Configuration 4)

A magnetic sensor, comprising: a first element part, the first element part including
a first magnetic layer, a first counter magnetic layer, and a first nonmagnetic layer provided between the first magnetic layer and the first counter magnetic layer, a direction from the first magnetic layer toward the first counter magnetic layer being along a first direction,
a first side magnetic layer, and
a second side magnetic layer, at least a part of the first magnetic element being between the first side magnetic layer and the second side magnetic layer in a second direction crossing the first direction,
a first magnetic member, a direction from the first side magnetic layer toward the first magnetic member being along the first direction, and
a second magnetic member, a direction from the second side magnetic layer toward the second magnetic member being along the first direction,
a direction from the first magnetic element toward a region between the first magnetic member and the second magnetic member being along the first direction,
the first magnetic layer and the first counter magnetic layer including a first material including Fe and Co, the first side magnetic layer and the second side magnetic layer including a second material, the second material including at least one of a third material including Fe and Ni or a fourth material, and the fourth material being amorphous or having crystallinity lower than crystallinity of the first material.

(Configuration 5)

The magnetic sensor according to Configuration 4, wherein the first side magnetic layer contacts the first magnetic element, or a distance between the first side magnetic layer and the first magnetic element is not more than 3 nm.

(Configuration 6)

The magnetic sensor according to Configuration 5, wherein the first side magnetic layer contacts the first magnetic layer and the first nonmagnetic layer.

(Configuration 7)

The magnetic sensor according to Configuration 6, wherein the first side magnetic layer contacts the first counter magnetic layer.

(Configuration 8)

The magnetic sensor according to one of Configurations 4 to 7, wherein the first element part further includes a first stacked magnetic layer, the first side magnetic layer is between a part of the first stacked magnetic layer and the first magnetic member, and the second side magnetic layer is between another part of the first stacked magnetic layer and the second magnetic member.

(Configuration 9)

A magnetic sensor, comprising: a first element part, the element part including a first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction, a first stacked magnetic layer, a first magnetic member, a direction from a part of the first stacked magnetic layer toward the first magnetic member being along the first direction, and a second magnetic member, a direction from another part of the first stacked magnetic layer toward the second magnetic member being along the first direction, a direction from the first magnetic element toward a region between the first magnetic member and the second magnetic member being along the first direction, the first magnetic element being between the first stacked magnetic layer and the region, the first magnetic layer and the first counter magnetic layer including a first material including Fe and Co, the first stacked magnetic layer including a second material, the second material including at least one of a third material including Fe and Ni or a fourth material, and the fourth material being amorphous or having crystallinity lower than crystallinity of the first material.

(Configuration 10)

The magnetic sensor according to one of Configurations 1 to 9, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is lower than the second value and lower than the third value.

(Configuration 11)

The magnetic sensor according to one of Configurations 1 to 9, wherein an electric resistance of the first magnetic element has a first value when a first magnetic field is applied to the first magnetic element, the electric resistance has a second value when a second magnetic field is applied to the first magnetic element, the electric resistance has a third value when a third magnetic field is applied to the first magnetic element, an absolute value of the first magnetic field is smaller than an absolute value of the second magnetic field, and smaller than an absolute value of the third magnetic field, a direction of the second magnetic field is opposite to a direction of the third magnetic field, and the first value is higher than the second value and higher than the third value.

(Configuration 12)

The magnetic sensor according to one of Configurations 1 to 9, wherein the first element part further includes a first conductive member, a first current including an AC component being supplied to the first conductive member, and the first conductive member overlaps the first magnetic element in the first direction.

(Configuration 13)

The magnetic sensor according to Configuration 12, wherein an electric resistance of the first magnetic element has a first value when a first current is supplied to the first conductive member, the electric resistance has a second value when a second current is supplied to the first conductive member, the electric resistance has a third value when a third current is supplied to the first conductive member, an absolute value of the first current is smaller than an absolute value of the second current and smaller than an absolute value of the third current, a direction of the second current is opposite to a direction of the third current, and the first value is lower than the second value, and lower than the third value.

(Configuration 14)

The magnetic sensor according to Configuration 12, wherein an electric resistance of the first magnetic element has a first value when a first current is supplied to the first conductive member, the electric resistance has a second value when a second current is supplied to the first conductive member, the electric resistance has a third value when a third current is supplied to the first conductive member, an absolute value of the first current is smaller than an absolute value of the second current and smaller than an absolute value of the third current, a direction of the second current is opposite to a direction of the third current, and the first value is higher than the second value, and higher than the third value.

(Configuration 15)

The magnetic sensor according to Configuration 13 or 14, wherein the electric resistance has a fourth value when a current does not flow through the first conductive member, and a ratio of an absolute value of a difference between the first value and the fourth value to the fourth value is not more than 0.01.

(Configuration 16)

The magnetic sensor according to one of Configurations 1 to 15, wherein the first magnetic element includes a first superimposition region overlapping the first magnetic member in the first direction, a second superimposition region overlapping the second magnetic member in the first direction, a length of the first superimposition region along the second direction is shorter than a length of the first structure along the second direction, and a length of the second superimposition region along the second direction is shorter than a length of the second structure along the second direction.

(Configuration 17)

The magnetic sensor according to one of Configurations 1 to 15, wherein the first magnetic element includes a first magnetic element end portion and a first magnetic element other end portion, the first magnetic element end portion is between the first structure and the first magnetic element other end portion, the first magnetic element other end portion is between the first magnetic element end portion and the second structure, the first magnetic member includes a first magnetic member end portion and a first magnetic member other end portion, the second magnetic member includes a second magnetic member end portion and a second magnetic member other end portion, the first magnetic member other end portion is between the first magnetic member end portion and the second magnetic member other end portion in the second direction, the second magnetic member end portion is between the first magnetic member other end portion and the second magnetic member other end portion in the second direction, the first magnetic element end portion overlaps the first magnetic member other end portion in the first direction, and the first magnetic element other end portion overlaps the second magnetic member end portion in the first direction.

(Configuration 18)

The magnetic sensor according to one of Configurations 1 to 15, wherein the first magnetic element includes a first magnetic element end portion and a first magnetic element other end portion, the first magnetic element end portion is between the first structure and the first magnetic element other end portion, the first magnetic element other end portion is between the first magnetic element end portion and the second structure, the first magnetic member includes a first magnetic member end portion and a first magnetic member other end portion, the second magnetic member includes a second magnetic member end portion and a second magnetic member other end portion, the first magnetic member other end portion is between the first magnetic member end portion and the second magnetic member other end portion in the second direction, the second magnetic member end portion is between the first magnetic member other end portion and the second magnetic member other end portion in the second direction, a position of the first magnetic element end portion in the second direction is between a position of the first magnetic member other end portion in the second direction and a position of the second magnetic member end portion in the second direction, and a position of the first magnetic element other end portion in the second direction is between the position of the first magnetic member other end portion in the second direction and the position of the second magnetic member end portion in the second direction.

(Configuration 19)

A magnetic sensor, comprising: a first element part, the first element part including a first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction, a first magnetic member, a direction from a part of the first magnetic layer toward the first magnetic member being along the first direction, and a second magnetic member, a direction from another part of the first magnetic layer toward the second magnetic member being along the first direction, a direction from the first counter magnetic layer toward a region between the first magnetic member and the second magnetic member being along the first direction, the first magnetic member including a first magnetic member end portion and a first magnetic member other end portion, the second magnetic member including a second magnetic member end portion and a second magnetic member other end portion, the first magnetic member other end portion being between the first magnetic member end portion and the second magnetic member other end portion in a second direction crossing the first direction, the second magnetic end portion being between the first magnetic member other end portion and the second magnetic member other end portion in the second direction, the first magnetic layer including a first magnetic layer end portion and a first magnetic layer other end portion, a position of the first magnetic layer end portion in the second direction being between a position of the first magnetic member end portion in the second direction and a position of the first magnetic member other end portion in the second direction, a position of the first magnetic layer other end portion in the second direction being between a position of the second magnetic member end portion in the second direction and a position of the second magnetic member other end portion in the second direction, the first counter magnetic layer including the first counter magnetic layer end portion and the first counter magnetic layer other end portion, a position of the first counter magnetic layer end portion in the second direction being between the position of the first magnetic member other end portion in the second direction and the position of the first magnetic layer other end portion in the second direction, and an electric resistance of the first magnetic element changing by an even function with respect to a magnetic field applied to the first magnetic element.

(Configuration 20)

The magnetic sensor according to Configuration 19, wherein the first element part further includes a first conductive member, a first current including an AC component being supplied to the first conductive member, and the first conductive member overlaps the first magnetic element in the first direction.

(Configuration 21)

The magnetic sensor according to Configuration 19 or 20, wherein the first element part further includes a first conductive portion, a second current being supplied to the first conductive portion, and the first conductive portion overlaps the first magnetic element in the first direction.

(Configuration 22)

The magnetic sensor according to one of Configurations 1 to 21, further comprising:

a second element part, a third element part, and a fourth element part, the first to fourth element parts being bridge-connected.

(Configuration 23)

An inspection device, comprising:

the magnetic sensor according to one of Configurations 1 to 22; and a processor being configured to process a signal output from the magnetic sensor.

According to the embodiments, a magnetic sensor and an inspection device which are possible to improve sensitivity can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, nonmagnetic layers, magnetic members, structures, conductive members, conductive portions, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising: a first element part, the first element part including
   a first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction,
   a first structure including a first side magnetic layer,
   a second structure including a second side magnetic layer, the first magnetic element being between the first structure and the second structure in a second direction crossing the first direction, the first magnetic element being separated from the first side magnetic layer and the second side magnetic layer,
   a first magnetic member, a direction from the first side magnetic layer toward the first magnetic member being along the first direction, and
   a second magnetic member, a direction from the second side magnetic layer toward the second magnetic member being along the first direction,
   a direction from the first magnetic element toward a region between the first magnetic member and the second magnetic member being along the first direction.

2. The magnetic sensor according to claim 1, wherein
   the first structure includes a first side counter magnetic layer and a firs side nonmagnetic layer,
   a direction from the first side magnetic layer toward the first side counter magnetic layer is along the first direction,
   the first side nonmagnetic layer is between the first side magnetic layer and the first side counter magnetic layer,
   the second structure includes a second side counter magnetic layer and a second side nonmagnetic layer,
   a direction from the second side magnetic layer toward the second side counter magnetic layer is along the first direction,
   the second side nonmagnetic layer is between the second side magnetic layer and the second side counter magnetic layer, and
   the first counter magnetic layer is between the first side counter magnetic layer and the second side counter magnetic layer.

3. The magnetic sensor according to claim 1, wherein
a distance along the second direction between the first magnetic layer and the first side magnetic layer is not less than 0.5 nm, and
a distance along the second direction between the first magnetic layer and the first side counter magnetic layer is not less than 0.5 nm.

4. The magnetic sensor according to claim 1, wherein
an electric resistance of the first magnetic element has a first value when a first magnetic field is applied to the first magnetic element,
the electric resistance has a second value when a second magnetic field is applied to the first magnetic element,
the electric resistance has a third value when a third magnetic field is applied to the first magnetic element,
an absolute value of the first magnetic field is smaller than an absolute value of the second magnetic field, and smaller than an absolute value of the third magnetic field,
a direction of the second magnetic field is opposite to a direction of the third magnetic field, and
the first value is lower than the second value and lower than the third value.

5. The magnetic sensor according to claim 1, wherein
an electric resistance of the first magnetic element has a first value when a first magnetic field is applied to the first magnetic element,
the electric resistance has a second value when a second magnetic field is applied to the first magnetic element,
the electric resistance has a third value when a third magnetic field is applied to the first magnetic element,
an absolute value of the first magnetic field is smaller than an absolute value of the second magnetic field, and smaller than an absolute value of the third magnetic field,
a direction of the second magnetic field is opposite to a direction of the third magnetic field, and
the first value is higher than the second value and higher than the third value.

6. The magnetic sensor according to claim 1, wherein
the first magnetic element includes
 a first superimposition region overlapping the first magnetic member in the first direction,
 a second superimposition region overlapping the second magnetic member in the first direction,
a length of the first superimposition region along the second direction is shorter than a length of the first structure along the second direction, and
a length of the second superimposition region along the second direction is shorter than a length of the second structure along the second direction.

7. The magnetic sensor according to claim 1, wherein
the first magnetic element includes a first magnetic element end portion and a first magnetic element other end portion,
the first magnetic element end portion is between the first structure and the first magnetic element other end portion,
the first magnetic element other end portion is between the first magnetic element end portion and the second structure,
the first magnetic member includes a first magnetic member end portion and a first magnetic member other end portion,
the second magnetic member includes a second magnetic member end portion and a second magnetic member other end portion,
the first magnetic member other end portion is between the first magnetic member end portion and the second magnetic member other end portion in the second direction,
the second magnetic member end portion is between the first magnetic member other end portion and the second magnetic member other end portion in the second direction,
the first magnetic element end portion overlaps the first magnetic member other end portion in the first direction, and
the first magnetic element other end portion overlaps the second magnetic member end portion in the first direction.

8. The magnetic sensor according to claim 1, wherein
the first magnetic element includes a first magnetic element end portion and a first magnetic element other end portion,
the first magnetic element end portion is between the first structure and the first magnetic element other end portion,
the first magnetic element other end portion is between the first magnetic element end portion and the second structure,
the first magnetic member includes a first magnetic member end portion and a first magnetic member other end portion,
the second magnetic member includes a second magnetic member end portion and a second magnetic member other end portion,
the first magnetic member other end portion is between the first magnetic member end portion and the second magnetic member other end portion in the second direction,
the second magnetic member end portion is between the first magnetic member other end portion and the second magnetic member other end portion in the second direction,
a position of the first magnetic element end portion in the second direction is between a position of the first magnetic member other end portion in the second direction and a position of the second magnetic member end portion in the second direction, and
a position of the first magnetic element other end portion in the second direction is between the position of the first magnetic member other end portion in the second direction and the position of the second magnetic member end portion in the second direction.

9. An inspection device, comprising:
the magnetic sensor according to claim 1; and
a processor being configured to process a signal output from the magnetic sensor.

10. The magnetic sensor according to claim 1, wherein
the first element part further includes a first conductive member, a first current including an AC component being supplied to the first conductive member, and
the first conductive member overlaps the first magnetic element in the first direction.

11. The magnetic sensor according to claim 10, wherein
an electric resistance of the first magnetic element has a first value when a first current is supplied to the first conductive member,
the electric resistance has a second value when a second current is supplied to the first conductive member,
the electric resistance has a third value when a third current is supplied to the first conductive member, an absolute value of the first current is smaller than an absolute value of the second current and smaller than an absolute value of the third current, a direction of the second current is opposite to a direction of the third current, and the first value is higher than the second value, and higher than the third value.

12. The magnetic sensor according to claim 10, wherein an electric resistance of the first magnetic element has a first value when a first current is supplied to the first conductive member, the electric resistance has a second value when a second current is supplied to the first conductive member, the electric resistance has a third value when a third current is supplied to the first conductive member, an absolute value of the first current is smaller than an absolute value of the second current and smaller than an absolute value of the third current, a direction of the second current is opposite to a direction of the third current, and the first value is lower than the second value, and lower than the third value.

13. The magnetic sensor according to claim 12, wherein the electric resistance has a fourth value when a current does not flow through the first conductive member, and a ratio of an absolute value of a difference between the first value and the fourth value to the fourth value is not more than 0.01.

14. A magnetic sensor, comprising: a first element part, the first element part including a first magnetic layer, a first counter magnetic layer, and a first nonmagnetic layer provided between the first magnetic layer and the first counter magnetic layer, a direction from the first magnetic layer toward the first counter magnetic layer being along a first direction, a first side magnetic layer, and a second side magnetic layer, at least a part of the first magnetic element being between the first side magnetic layer and the second side magnetic layer in a second direction crossing the first direction, a first magnetic member, a direction from the first side magnetic layer toward the first magnetic member being along the first direction, and a second magnetic member, a direction from the second side magnetic layer toward the second magnetic member being along the first direction, a direction from the first magnetic element toward a region between the first magnetic member and the second magnetic member being along the first direction, the first magnetic layer and the first counter magnetic layer including a first material including Fe and Co, the first side magnetic layer and the second side magnetic layer including a second material, the second material including at least one of a third material including Fe and Ni or a fourth material, and the fourth material being amorphous or having crystallinity lower than crystallinity of the first material.

15. The magnetic sensor according to claim 14, wherein the first element part further includes a first stacked magnetic layer, the first side magnetic layer is between a part of the first stacked magnetic layer and the first magnetic member, and the second side magnetic layer is between another part of the first stacked magnetic layer and the second magnetic member.

16. The magnetic sensor according to claim 14, wherein the first side magnetic layer contacts the first magnetic element, or a distance between the first side magnetic layer and the first magnetic element is not more than 3 nm.

17. The magnetic sensor according to claim 16, wherein the first side magnetic layer contacts the first magnetic layer and the first nonmagnetic layer.

18. The magnetic sensor according to claim 17, wherein the first side magnetic layer contacts the first counter magnetic layer.

19. A magnetic sensor, comprising: a first element part, the element part including a first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction, a first stacked magnetic layer, a first magnetic member, a direction from a part of the first stacked magnetic layer toward the first magnetic member being along the first direction, and a second magnetic member, a direction from another part of the first stacked magnetic layer toward the second magnetic member being along the first direction, a direction from the first magnetic element toward a region between the first magnetic member and the second magnetic member being along the first direction, the first magnetic element being between the first stacked magnetic layer and the region, the first magnetic layer and the first counter magnetic layer including a first material including Fe and Co, the first stacked magnetic layer including a second material, the second material including at least one of a third material including Fe and Ni or a fourth material, and the fourth material being amorphous or having crystallinity lower than crystallinity of the first material.

* * * * *

UNITED STATES PATENT AND TRADEMARK OFFICE
CERTIFICATE OF CORRECTION

PATENT NO. : 11,493,571 B2
APPLICATION NO. : 17/395623
DATED : November 8, 2022
INVENTOR(S) : Hitoshi Iwasaki It is certified that error appears in the above-identified patent and that said Letters Patent is hereby corrected as shown below:

In the Claims

Claim 2, Column 30, Line 51, "firs" should read as --first--.

Signed and Sealed this
Sixteenth Day of May, 2023

*Katherine Kelly Vidal*

Katherine Kelly Vidal
*Director of the United States Patent and Trademark Office*